US011524061B2

(12) United States Patent
Selvaraj et al.

(10) Patent No.: US 11,524,061 B2
(45) Date of Patent: Dec. 13, 2022

(54) POULTRY VACCINE FOR CLOSTRIDIUM PERFRINGENS

(71) Applicants: UNIVERSITY OF GEORGIA RESEARCH FOUNDATION, INC., Athens, GA (US); THE OHIO STATE UNIVERSITY, Columbus, OH (US)

(72) Inventors: Ramesh Kumar Selvaraj, Bogart, GA (US); Gabriel Akerele, Athens, GA (US); Sankar Renu, Wooster, OH (US); Renukaradhya J. Gourapura, Wooster, OH (US)

(73) Assignees: UNIVERSITY OF GEORGIA RESEARCH FOUNDATION, INC, Athens, GA (US); THE OHIO STATE UNIVERSITY, Columbus, OH (US)

( * ) Notice: Subject to any disclaimer, the term of this patent is extended or adjusted under 35 U.S.C. 154(b) by 0 days.

(21) Appl. No.: 17/167,893

(22) Filed: Feb. 4, 2021

(65) Prior Publication Data
US 2021/0236617 A1 Aug. 5, 2021

Related U.S. Application Data

(60) Provisional application No. 62/969,741, filed on Feb. 4, 2020.

(51) Int. Cl.
*A61K 39/08* (2006.01)
*A61K 39/00* (2006.01)

(52) U.S. Cl.
CPC ........ *A61K 39/08* (2013.01); *A61K 2039/542* (2013.01); *A61K 2039/552* (2013.01)

(58) Field of Classification Search
None
See application file for complete search history.

(56) References Cited

FOREIGN PATENT DOCUMENTS

| WO | 2019/035963 | 2/2019 | |
|---|---|---|---|
| WO | WO-2019238684 A1 * | 12/2019 | ............. A61K 38/28 |

OTHER PUBLICATIONS

Rose and Hesketh, "Immunity to Coccidiosis: T-lymphocyte- or B-lymphocyte-Deficient animals," 1979, Infection and Immunity; 26(2):630-637.
Sadeghi et al., "Effects of dietary supplementation of Ferulago angulata (Schlecht.) Boiss powder on growth performance, carcass characteristics, and gut microflora and pH in broiler chicks," 2016, Comparative Clinical Pathology; 25(2):257-263. https://doi.org/10.1007/s00580-015-2175-z.
Saleh et al., "Clinicopathological and immunological studies on toxoids vaccine as a successful alternative in controlling clostridial infection in broilers," 2011, Anaerobe; 17(6):426-430.
Savva et al., "Molecular Architecture and Functional Analysis of NetB, a Pore-forming Toxin from Clostridium perfringens," 2013, J Biol Chem; 288(5):3512-22.
Sengupta et al., "Comparative Proteomic Analysis of Extracellular Proteins of Clostridium perfringens Type A and Type C Strains," 2010, Infection and Immunity; 78(9):3957-3968.
Shanmugasundaram et al., "Effect of *Salmonella* infection on cecal tonsil regulatory T cell properties in chickens," 2015, Poult Sci; 94(8):1828-35.
Shojadoost et al., "The successful experimental induction of necrotic enteritis in chickens by Clostridium perfringens: A critical review," 2012, Veterinary Research; 43(1):74.
Si et al., "Quantification of cell proliferation and alpha-toxin gene expression of Clostridium perfringens in the development of necrotic enteritis in broiler chickens," 2007, Appl Environ Microbiol; 73:7110-7113.
Tanaka et al., "Splenic adherent cells, stimulated in vitro, induce the reactive formation of lymphoid follicles and germinal centres in draining lymph nodes after subcutaneous transfusion into syngeneic mice," 1998, Journal of Anatomy; 193(1):49-59.
Thompson et al., "Live attenuated vaccine-based control of necrotic enteritis of broiler chickens," 2006, Veterinary Microbiology; 113(1-2):25-34.
Timbermont et al., "Necrotic enteritis in broilers: an updated review on the pathogenesis," 2011, Avian Pathol; 40(4):341-7.
Torres et al., "Amphiphilic polyanhydrides for protein stabilization and release," 2007, Biomaterials; 28:108-116.
Uzal et al., "Clostridium Perfringens Toxins Involved in Mammalian Veterinary Diseases," 2014, Open Toxinology J, 2: 24-42.
Wade and Keyburn, "The true cost of necrotic enteritis" Accessed on the internet at www.poultryworld.net/Meat/Articles/2015/10/The-true-cost-of-necrotic-enteritis-2699819W/ on Jan. 23, 2020, 2015, PoultryWorld Oct. 9, 2015.
Wilde et al., "*Salmonella*-vectored vaccine delivering three Clostridium perfringens antigens protects poultry against necrotic enteritis," 2019, PLoS One Feb. 12, 2019;14(2):e0197721. doi: 10.1371/journal.pone.0197721. eCollection 2019.
Wu et al., "Two necrotic enteritis predisposing factors, dietary ?shmeal and Eimeria infection, induce large changes in the cecal microbiota of broiler chickens," 2014, Vet Microbiol; 169:188-197.
Yata and Ghosh, "Synthesis and characterization of a novel chitosan-based *E. coli* cytosine deaminase nanocomposite for potential application in prodrug enzyme therapy," 2011, Biotechnol Lett; 33(1):153-157.

(Continued)

Primary Examiner — Brian Gangle
(74) Attorney, Agent, or Firm — Mueting Raasch Group

(57) ABSTRACT

The present disclosure relates to nanoparticle compositions for use as vaccines against *Clostridium perfringens* in poultry which causes necrotic enteritis in poultry. Such compositions include one or more *Clostridium perfringens* extracellular proteins entrapped in a polyanhydride or chitosan nanoparticle. The one or more *Clostridium perfringens* extracellular proteins may include one or more *Clostridium perfringens* toxins, such as, for example, alpha toxin (CPA), beta toxin (CPB), epsilon toxin (ETX), iota toxin (ITX), perfringolysin O (PFO), enterotoxin (CPE), beta2 toxin (CPB2), or NetB toxin. In some aspects, the composition further includes a *Salmonella enteritidis* flagellar protein. The present invention also includes methods for the oral delivery of one or more *Clostridium perfringens* extracellular proteins to the mucosal membrane of the intestinal tract of a bird of the order Galliformes.

19 Claims, 34 Drawing Sheets

(56) References Cited

OTHER PUBLICATIONS

Zhao et al., "Preparation and Efficacy of a Live Newcastle Disease Virus Vaccine Encapsulated in Chitosan Nanoparticles," 2012, PLoS ONE; 7(12):1-11. https://doi.org/10.1371/journal.pone.0053314.
Zhao et al., "Nanoparticle vaccines," 2014, Vaccines; 32:327-337.
Zhao et al., "Preparation and efficacy of Newcastle disease virus DNA vaccine encapsulated in chitosan nanoparticles," 2014, Int J Nanomedicine; 9:389-402.
Zhao et al., "Chitosan-coated poly(lactic-co-glycolic) acid nanoparticles as an efficient delivery system for Newcastle disease virus DNA vaccine," 2014, Int J Nanomedicine; 9:4609-19.
Powerpoint presented at International Production and Processing Expo (IPPE) meeting held Feb. 12-14, 2019, in Atlanta, GA.
Abstract ("Physiochemical characteristics and immunogenicity of chitosan nanoparticles loaded with extracellular proteins of C. perfringens and *Salmonella flagella* proteins") submitted for the International Production and Processing Expo (IPPE) meeting held Jan. 28-30, 2020 in Atalanta, GA, Ramadan et al.
Abstract ("Mucosal immunity of broilers vaccinated with an oral polyanhydride-nanoparticle based Clostridium perfringens vaccine expressing *Salmonella enterica* flagella") submitted for the International Production and Processing Expo (IPPE) meeting held anuary 28-30, 2020 in Atalanta, GA, Ramadan et al.
Acevedo-Villanueva et al., "Efficacy of a nanoparticle vaccine administered in-ovo against *Salmonella* in broilers," PLoS One. Apr. 6, 2021;16(4):e0247938. doi: 10.1371/journal.pone.0247938. eCollection 2021.
Acevedo-Villanueva et al., "*Salmonella chitosan* nanoparticle vaccine administration is protective against *Salmonella enteritidis* in broiler birds," PLoS One. Nov. 16, 2021;16(11):e0259334. doi: 10.1371/journal.pone.0259334. eCollection 2021.
Acevedo-Villanueva et al., "Efficacy of chitosan-based nanoparticle vaccine administered to broiler birds challenged with *Salmonella*," PLoS One. Apr. 24, 2020;15(4):e0231998. doi: 10.1371/journal.pone.0231998. eCollection 2020.
Akerele et al., "In vitro characterization and immunogenicity of chitosan nanoparticles loaded with native and inactivated extracellular proteins from a field strain of Clostridium perfringens associated with necrotic enteritis," Vet Immunol Immunopathol. Jun. 2020;224:110059. doi: 10.1016/j.vetimm.2020.110059. Epub Apr. 30, 2020.
Alam and Dwivedi, "Putative function of hypothetical proteins expressed by Clostridium perfringens type A strains and their protective efficacy in mouse model," 2016, Infection, Genetics and Evolution; 44:147-156.
Basu and Domb, "Recent Advances in Polyanhydride Based Biomaterials," 2018, Adv Mater; 30:e1706815. doi: 10.1002/adma.201706815.
Binjawadagi et al., "Adjuvanted poly(lactic-co-glycolic) acid nanoparticle-entrapped inactivated porcine reproductive and respiratory syndrome virus vaccine elicits cross-protective immune response in pigs," 2014, International Journal of Nanomedicine 9:679-694.
Binjawadagi et al., "An innovative approach to induce cross-protective immunity against porcine reproductive and Yespiratory syndrome virus in the lungs of pigs through adjuvanted nanotechnology-based vaccination," 2014, International Journal of Nanomedicine 9:1519-1535.
Bokori-Brown et al., "Molecular basis of toxicity of Clostridium perfringens epsilon toxin," 2011, Febs J. Dec. 2011;278(23):4589-601. doi: 10.1111/j.1742-4658.2011.08140.x.
Crouch et al., "Safety and efficacy of a maternal vaccine for the passive protection of broiler chicks against necrotic enteritis Safety and efficacy of a maternal vaccine for the passive protection of broiler chicks against necrotic enteritis," 2010, Avian Pathol; 39(6):489-97.
Da Costa et al., "Protection against avian necrotic enteritis after immunisation with NetB geneticor formaldehyde toxoids," 2013, Vaccine 31:4003-4008.
Dahiya et al., "Dietary glycine concentration affects intestinal Clostridium perfringens and lactobacilli populations in broiler chickens," 2005, Poult Sci. 84(12):1875-85. doi: 10.1093/ps/84.12.1875.
Dhakal et al., "Mucosal immunity and Protective efficacy of intranasal inactivated influenza Vaccine is improved by chitosan nanoparticle Delivery in Pigs," 2018, Front Immunol; 9:934.
Dhakal et al., "Nanoparticle-based vaccine development and evaluation against viral infections in pigs," 2019, Vet Res 50:90. https://doi.org/10.1186/s13567-019-0712-5.
Eby et al., "Use of a Toxin Neutralization Assay To Characterize the Serologic Response to Adenylate Cyclase Toxin after Infection with Bordetella pertussis," 2017, Clinical and Vaccine Immunology, 24(1): e00370-16.
Elwinger et al., "Factors affecting the incidence of necrotic enteritis, caecal carriage of Clostridium perfringens and bird performance in broiler chicks," 1992, Acta Veterinaria Scandinavica; 33:369-378.
Engstrom et al., "Molecular typing of isolates of Clostridium perfringens from healthy and diseased poultry," 2003, Vet Microbiol; 94(3):225-235.
Fasina and Lillehoj, "Characterization of intestinal immune response to Clostridium perfringens infection in broiler chickens," 2019, Poult Sci; 98(1):188-198.
Foley et al., "Population dynamics of *Salmonella enterica* serotypes in commercial egg and poultry production," 2011, Applied and Environmental Microbiology; 77(13):4273-4279.
Gupta et al., "Flagellin a toll-like receptor 5 agonist as an adjuvant in chicken vaccines," 2014, Clin Vaccine Immunol. Mar. 2014; 21(3):261-70. doi: 10.1128/CVI.00669-13.
Han et al., "Immune Response to *Salmonella enteritidis* Infection in Broilers Immunized Orally With Chitosan-Based *Salmonella* Subunit Nanoparticle Vaccine," Front Immunol. May 19, 2020;11:935. doi: 10.3389/fimmu.2020.00935. eCollection 2020.
Han et al., "Mannose-Modified Chitosan-Nanoparticle-Based *Salmonella* Subunit OralVaccine-Induced Immune Response and Efficacy in a Challenge Trial in Broilers," Vaccines (Basel). Jun. 11, 2020;8(2):299. doi: 10.3390/vaccines8020299.
Han et al., "Temporal dynamics of innate and adaptive immune responses in broiler birds to oral delivered chitosan nanoparticle-based *Salmonella* subunit antigens," Vet Immunol Immunopathol. Oct. 2020;228:110111. doi: 10.1016/j.vetimm.2020.110111. Epub Aug. 17, 2020.
Hoshi et al., "Formation of lymph follicles and germinal centres in draining lymph nodes after local injection of phytohemagglutinin and lipopolysaccharide in mice," 1984, Archivum Histogicum Japonicum; 47: 505-518.
Hoshi et al., "Formation of lymph follicles in draining lymph nodes after local injection of various antigenic substances in mice," 1986, Archivum Histogicum Japonicum; 49: 25-37.
Hou et al., "Chitosan-based nanoparticles as a sustained protein release carrier for tissue engineering applications," 2012, J Biomed Mater Res A. Apr. 2012;100(4):939-47. doi: 10.1002/jbm.a.34031. Epub Jan. 24, 2012.
Hu et al., "Nanoparticle-detained toxins for safe and effective vaccination," 2013, Nature Nanotechnology; 8(12):933-8.
Huang et al., "Intranasal immunization with chitosan/pCAGGS-flaA nanoparticles inhibits Campylobacter jejuni in a White Leghorn model," 2010, J Biomed Biotechnol; 2010:589476.
Kaldhusdal et al., "Epidemiologic aspects of necrotic enteritis in broiler chickens—disease occurrence and production performance," 2016, Avian Pathol; 45(3):271-274.
Keyburn et al., "NetB, a new toxin that is associated with avian necrotic enteritis caused by Clostridium perfringens," 2008, PLoS Pathogens; 4(2):e26.
Kim and Jang, "Antigen targeting to M cells for enhancing the efficacy of mucosal vaccines," 2014, Experimental and Molecular Medicine; 46(3):e85-8.
Komoriya et al., "Flagellar proteins and type III-exported virulence factors are the predominant proteins secreted into the culture media of *Salmonella typhimurium*," 1999, Molecular Microbiology; 34(4):767-779.

(56) References Cited

OTHER PUBLICATIONS

Kulkarni et al., "Clostridium perfringens Antigens Recognized by Broiler Chickens Immune to Necrotic Enteritis," 2006, Clinical and Vaccine Immunology 13(12):1358-1362.

Kulkarni et al., "Immunization of Broiler Chickens against Clostridium perfringens-Induced Necrotic Enteritis," 2007, Clinical and Vaccine Immunology; 14(9):1070-1077.

Lanckriet et al., "Variable protection after vaccination of broiler chickens against necrotic enteritis using supernatants of different Clostridium perfringens strains," 2010, Vaccine; 28(36):5920-5923.

Lepp et al., "Identification of Novel Pathogenicity Loci in Clostridium perfringens Strains That Cause Avian Necrotic Enteritis," 2010, Plos ONE 5(5):e10795.

Li et al., "Synthesis and characterization of chitosan derivatives with dual-antibacterial functional groups," 2015, International Journal of Biological Macromolecules; 75:378-387.

Mishra and Smyth, "Oral vaccination of broiler chickens against necrotic enteritis using a non-virulent NetB positive strain of Clostridium perfringens type A," 2017, Vaccine. Dec. 14, 2017;35(49 Pt B):6858-6865. doi: 10.1016/j.vaccine.2017.10.030. Epub Nov. 1, 2017.

Mot et al., "Progress and problems in vaccination against necrotic enteritis in broiler chickens," 2014, Avian Pathol;43(4):290-300. doi: 10.1080/03079457.2014.939942.

Ngundi et al., "Comparison of Three Anthrax Toxin Neutralization Assays," 2010, Clin Vaccine Immunol; 17(6):895-903.

Paiva and McElroy, "Necrotic enteritis: Applications for the poultry industry," 2014, Journal of Applied Poultry Research; 23(3):557-566.

Pan et al., "Flagellin from recombinant attenuated *Salmonella enterica* serovar Typhimurium reveals a fundamental role in chicken innate immunity," 2012, Clin. Vaccine Immunol; 19:304-312.

Pan et al., "The Effect of Polymeric Nanoparticles on Biocompatibility of Carrier Red Blood Cells," 2016, PLoS One; 11(3):e0152074.

Park et al., "Optimization of Ammonium Sulfate Concentration for Purification of Colorectal Cancer Vaccine Candidate Recombinant Protein GA733-FcK Isolated from Plants," 2015, Frontiers in Plant Science; 6:1040.

Petersen et al., "Activation of innate immune responses in a pathogen-mimicking manner by amphiphilic polyanhydride nanoparticle adjuvants," 2011, Biomaterials; 32(28):6815-6822.

Prabaharan and Mano, "Chitosan-based particles as controlled drug delivery systems," 2005, Drug Deliv Rev; 12(1):41-57.

Pratten and Lloyd, "Pinocytosis and phagocytosis: the effect of size of a particulate substrate on its mode of capture by rat peritoneal macrophages cultured in vitro," 1986, Biochim Biophys Acta; 881(3):307-13.

Renu et al., "Surface engineered polyanhydride-based oral *Salmonella* subunit nanovaccine for poultry," Int J Nanomedicine. Nov. 30, 2018;13:8195-8215. doi: 10.2147/IJN.S185588. eCollection 2018.
Renu et al., "Oral Deliverable Mucoadhesive Chitosan-*Salmonella* Subunit Nanovaccine for Layer Chickens," Int J Nanomedicine. Feb. 3, 2020;15:761-777. doi: 10.2147/IJN.S238445. eCollection 2020.
Renu et al., "Chitosan-adjuvanted *Salmonella* subunit nanoparticle vaccine for poultry delivered through drinking water and feed," Carbohydr Polym. Sep. 1, 2020;243:116434. doi: 10.1016/j.carbpol.2020.116434. Epub May 19, 2020.

* cited by examiner

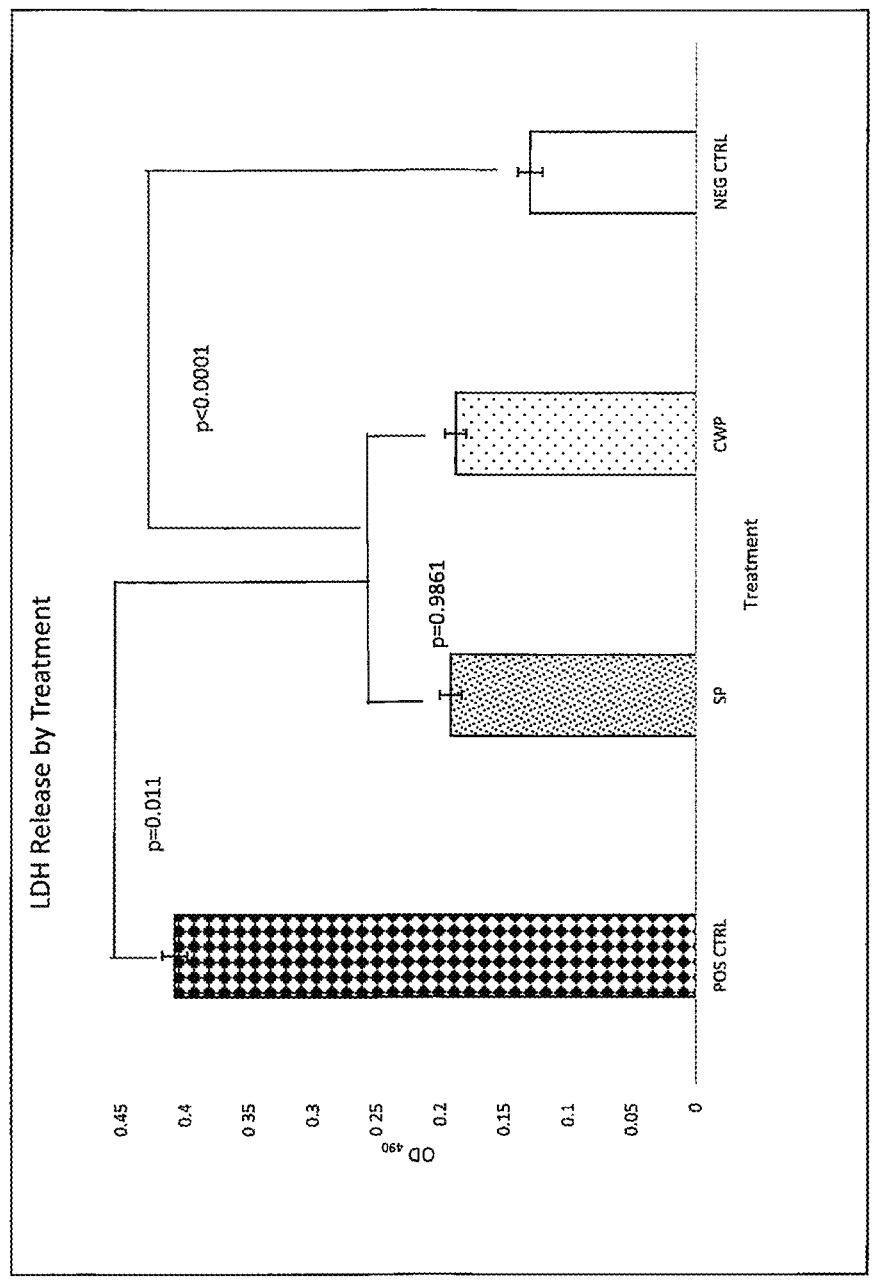

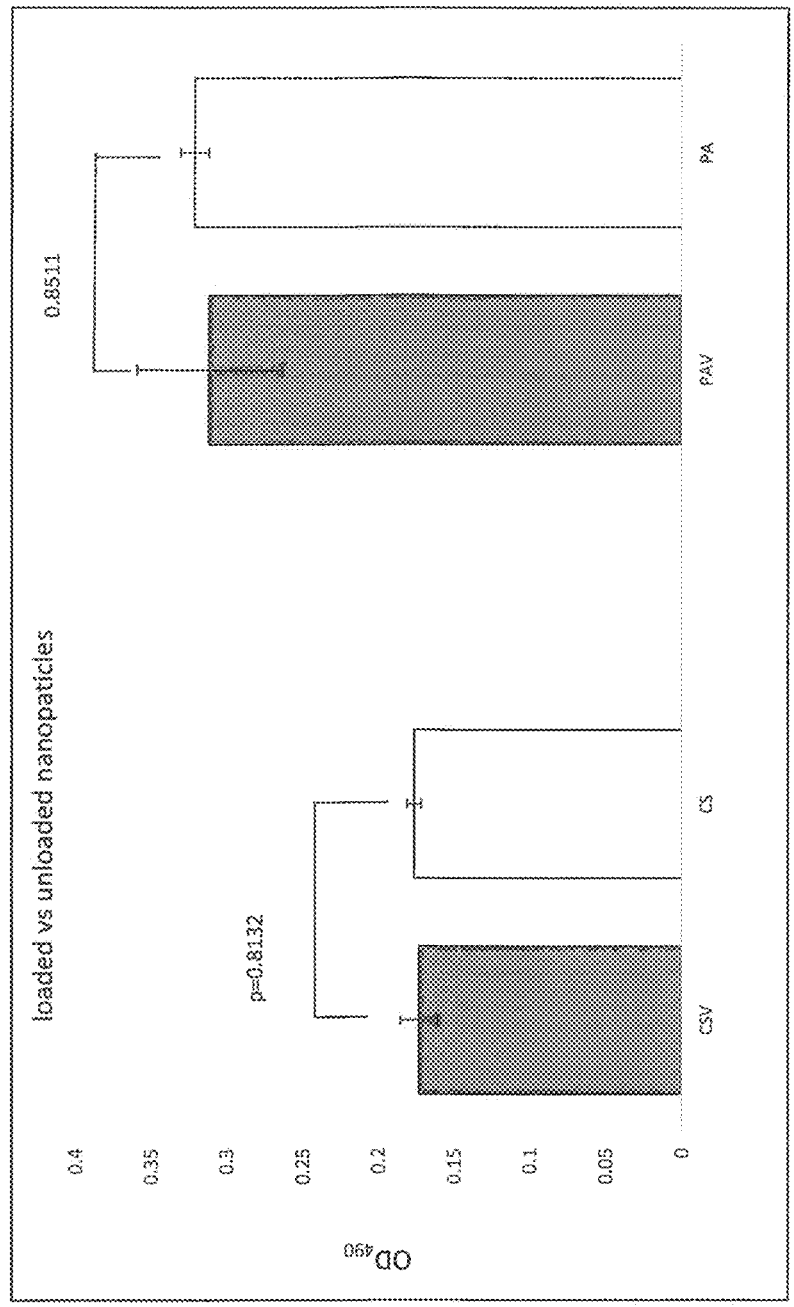

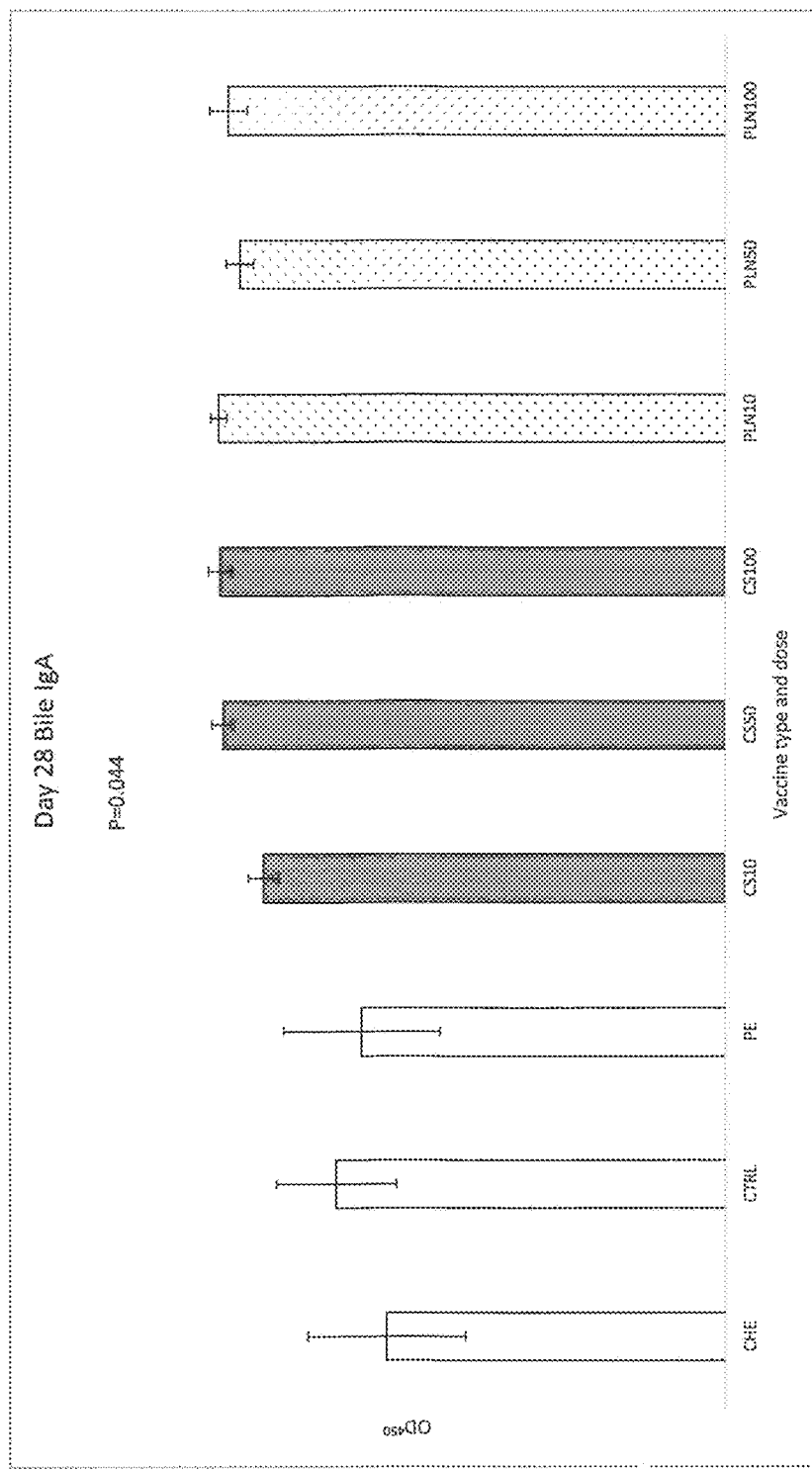

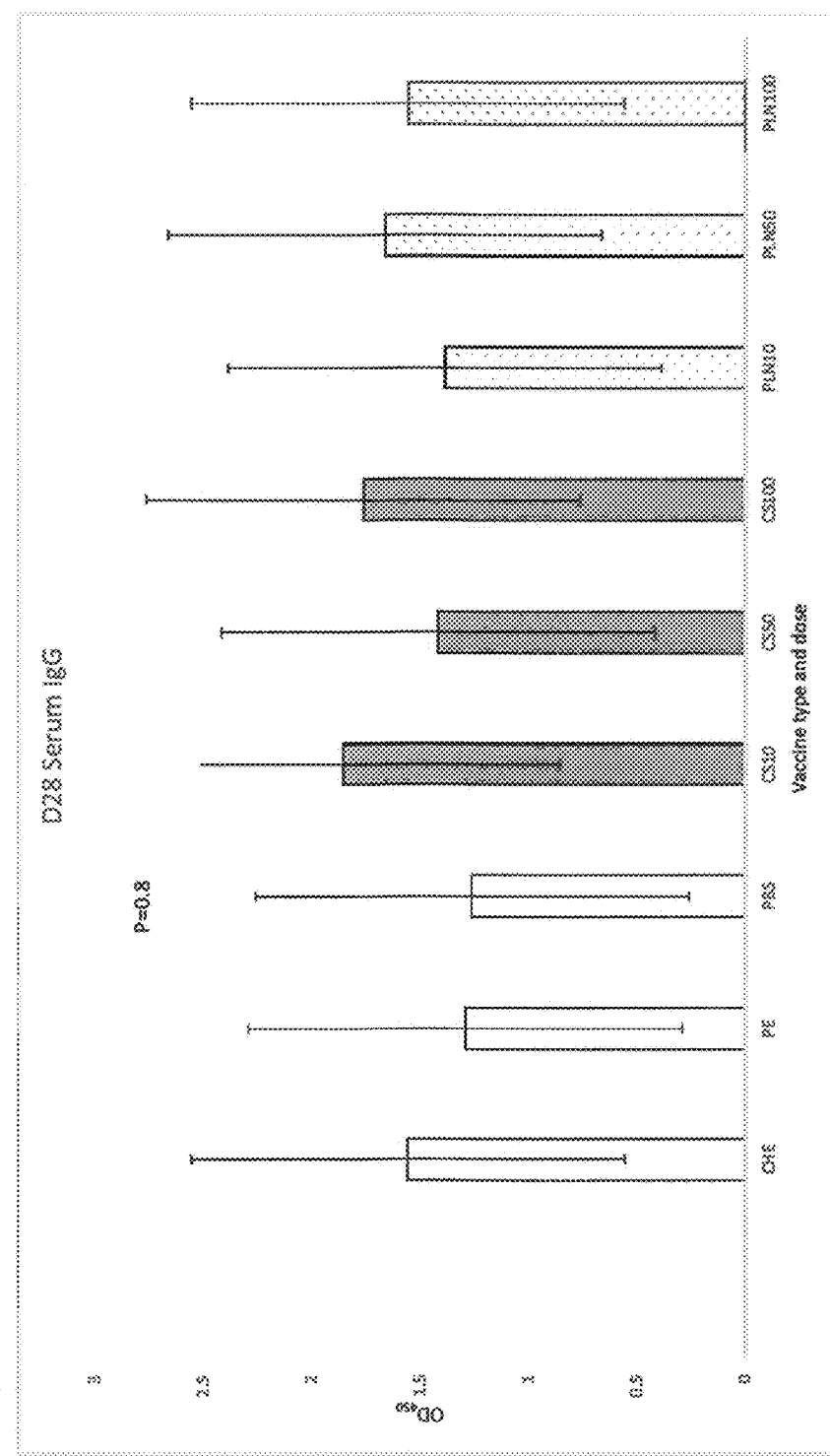

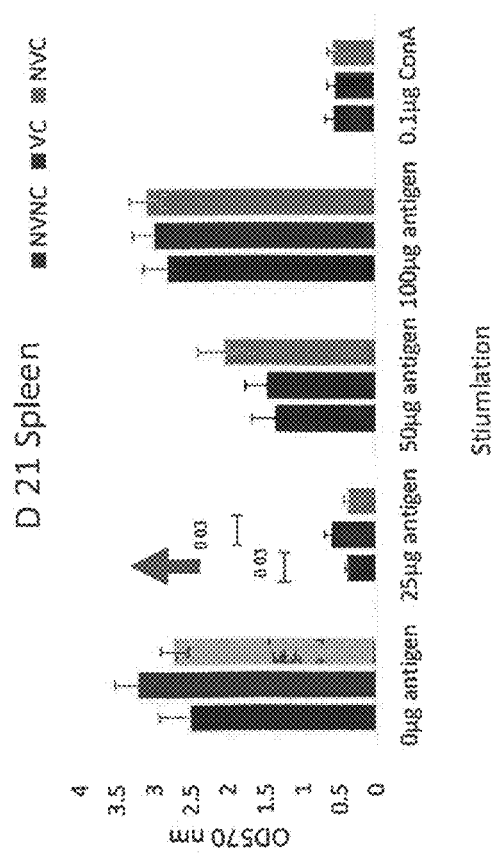

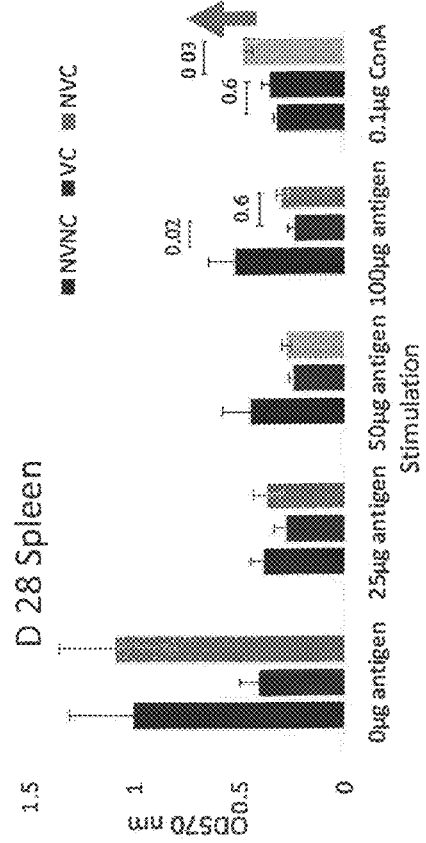

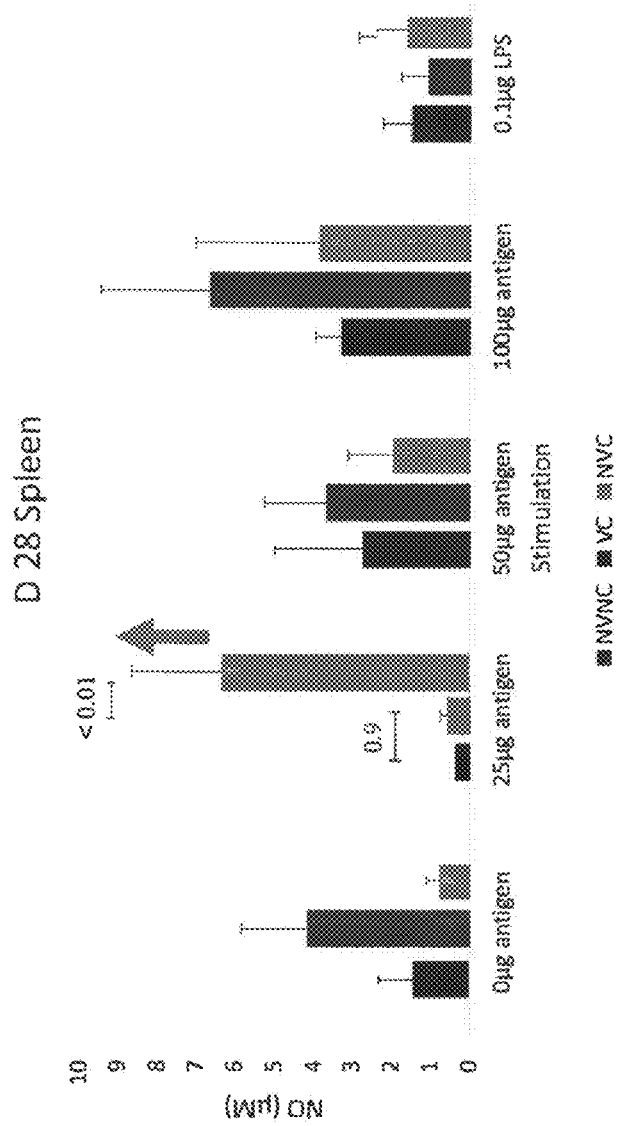

POULTRY VACCINE FOR CLOSTRIDIUM PERFRINGENS

CONTINUING APPLICATION DATA

This application claims the benefit of U.S. Provisional Application Ser. No. 62/969,741, filed Feb. 4, 2020, which is incorporated by reference herein.

GOVERNMENT FUNDING

This invention was made with government support under Grant No. 58-6040-8-034 awarded by the United States Department of Agriculture/Agricultural Research Service (USDA/ARS). The government has certain rights in the invention.

BACKGROUND

Necrotic enteritis (NE) is a common bacterial disease of poultry, estimated to cost the international poultry industry as much as 5-6 billion USD annually in control measures and productivity losses (Wade and Keyburn, "The True Cost of Necrotic Enteritis," *Poultry World*, 2015). Necrotic enteritis is known to affect broilers, laying hens, turkeys, and quail. Clinical infections occur when *Clostridium perfringens* proliferates in the small intestine and produces exotoxins that damage the intestinal epithelium, resulting in necrotic lesions. The clinical form is most commonly seen in two to five-week-old broilers, where symptoms, including severe depression, decreased appetite, diarrhea, closed eyes, and ruffled feathers, are short-lived because affected birds die quickly. The chronic, subclinical form of the disease often goes undetected, causing large reductions in growth and feed conversion rates, and significant economic loss. Traditionally, control of necrotic enteritis has been by supplementing feed with sub-therapeutic doses of antibiotics. However, as the poultry industry increasingly turns towards the removal of antibiotic growth promoters from feed, clinical and subclinical necrotic enteritis infections are increasing in occurrence and severity. There are currently no licensed vaccines against *Clostridium perfringens* which causes necrotic enteritis in poultry. There is a need for effective vaccines against *Clostridium perfringens*, including vaccines that can be administered orally.

SUMMARY OF THE INVENTION

The present invention includes compositions of one or more *Clostridium perfringens* extracellular proteins and a polyanhydride or chitosan nanoparticle.

In some aspects, the one or more *Clostridium perfringens* extracellular proteins are from a *Clostridium perfringens* culture supernatant.

In some aspects, the *Clostridium perfringens* includes type A, type B, type C, type D, or type E *Clostridium perfringens*.

In some aspects, the one or more *Clostridium perfringens* extracellular proteins includes native polypeptides. In some aspects, the one or more *Clostridium perfringens* extracellular proteins include inactivated polypeptides.

In some aspects, the one or more *Clostridium perfringens* extracellular proteins include one or more *Clostridium perfringens* toxins. In some aspects, the toxin includes alpha toxin (CPA), beta toxin (CPB), epsilon toxin (ETX), iota toxin (ITX), perfringolysin 0 (PFO), enterotoxin (CPE), beta2 toxin (CPB2), or NetB toxin.

In some aspects, the nanoparticle includes polyanhydride. In some aspects, the nanoparticle includes chitosan.

In some aspects, the one or more *Clostridium perfringens* extracellular polypeptides are entrapped within the nanoparticle.

In some aspects, the nanoparticle is about 150 to 200 nanometers is diameter.

In some aspects, the composition further includes a *Salmonella enteritidis* flagellar protein. In some aspects, the *Salmonella enteritidis* flagellar protein is present on the surface of the nanoparticle. In some aspects, the *Salmonella enteritidis* flagellar protein is conjugated to the surface of the nanoparticle.

In some aspects, the composition further includes an adjuvant.

The present invention includes a pharmaceutical composition including a nanoparticle composition as described herein and a pharmaceutically acceptable carrier.

The present invention includes a vaccine including a nanoparticle composition as described herein.

In some aspects, a nanoparticle composition, pharmaceutical composition, or vaccine as described herein is formulated for oral delivery.

The present invention includes a method of generating an immune response to *Clostridium perfringens* in a subject, the method including administering a nanoparticle composition, pharmaceutical composition, or vaccine as described herein to the subject. In some aspects, the subject includes a bird of the order Galliformes. In some aspects, the bird of the order Galliformes includes a chicken or turkey. In some aspects, the immune response includes a humoral and/or a cellular immune response. In some aspects, administration includes oral delivery. In some aspects, oral delivery includes delivery by food. In some aspects, oral delivery includes delivery by drinking water.

The present invention includes a method for protecting a bird of the order Galliformes against necrotic enteritis, the method including administering to the bird a nanoparticle composition, pharmaceutical composition, or vaccine as described herein. In some aspects, administration includes oral delivery. In some aspects, oral delivery includes delivery by food. In some aspects, oral delivery includes delivery by drinking water.

The present invention includes a method for delivery of one or more *Clostridium perfringens* extracellular proteins to the mucosal membrane of the intestinal tract of a bird of the order Galliformes, the method including the oral administration to the bird of a nanoparticle composition, pharmaceutical composition, or vaccine as described herein to the bird. In some aspects, oral delivery includes delivery by food. In some aspects, oral delivery includes delivery by drinking water.

BRIEF DESCRIPTION OF THE FIGURES

FIG. 3A cumulative antigen release for polyanhydride vaccine and chitosan vaccine. FIG. 3B presents antigen release for polyanhydride vaccine over pH range of 2.5 to 8. FIG. 3C presents antigen release for chitosan vaccine over pH range of 2.5 to 8.

FIGS. 4A and 4B. Biosafety in LDH assay using LMH cells. Statistical analysis done with SAS general linear model. Alpha was set at 0.05. FIG. 4A presents LDH release by treatment. FIG. 4B presents results with loaded versus unloaded nanoparticles.

FIGS. 5A and 5B. Assessment of safety and immunogenicity. Treatments: Ch-Np Dose 10 μg (CS10); Ch-Np Dose 50 μg (CS50); Ch-Np Dose 100 μg (CS100); P-Np Dose 10 μg (PLN10); P-Np Dose 50 μg (PLN50); P-Np Dose 100 μg (PLN100); empty chitosan nanoparticles (CHE); empty polyanhydride nanoparticles (PE); and PBS control (CTRL). FIG. 5A shows day 28 bile IgA. FIG. 5B shows day 28 serum IgG. Statistical analysis done with SAS general linear model. Alpha was set at 0.05.

FIG. 6A shows SDS-PAGE (10%) analysis of band intensity against 37 kDA, 50 kDa, and 42 kDa polypeptides. FIG. 6B shows band intensities against the 37 kDA polypeptide. FIG. 6C shows band intensities against the 50 kDA polypeptide. FIG. 6D shows band intensities against the 42 kDA polypeptide.

FIG. 14A is a schematic of a nanoparticle. FIG. 14B shows the chemical structure of chitosan, a derivative of chitin. As shown in FIG. 14C, chitosan is cationic and when combined with a polyanion tripolyphosphate can cross the gut to submucosa.

As shown in FIG. 17A, vaccinated birds had smaller lesions and less mortality than non-vaccinated birds. As shown in FIG. 17B, there was no effect of treatment on weight gain at one- and two-weeks post infection.

As shown in FIG. 18A, vaccinated birds had smaller lesions and less mortality than non-vaccinated birds. As shown in FIG. 18B, vaccinated birds had greater feed intake than non-vaccinated birds.

As shown in FIG. 19A, LMH cytotoxicity in serum and ECP was lower in non-vaccinated, challenge birds. As shown in FIG. 19B, LMH cytotoxicity in bile and ECP was higher in non-vaccinated, challenge birds.

FIG. 20A to 20C. Recall response. FIG. 20A shows results from D18 spleen. FIG. 20B shows results from D21 spleen. FIG. 20C shows results from D28 spleen.

FIG. 24A shows NO production at 18 dph. FIG. 24B shows NO production at 28 dph.

FIG. 25. Spleen nitric oxide production.

DETAILED DESCRIPTION OF ILLUSTRATIVE EMBODIMENTS

Figure 1:
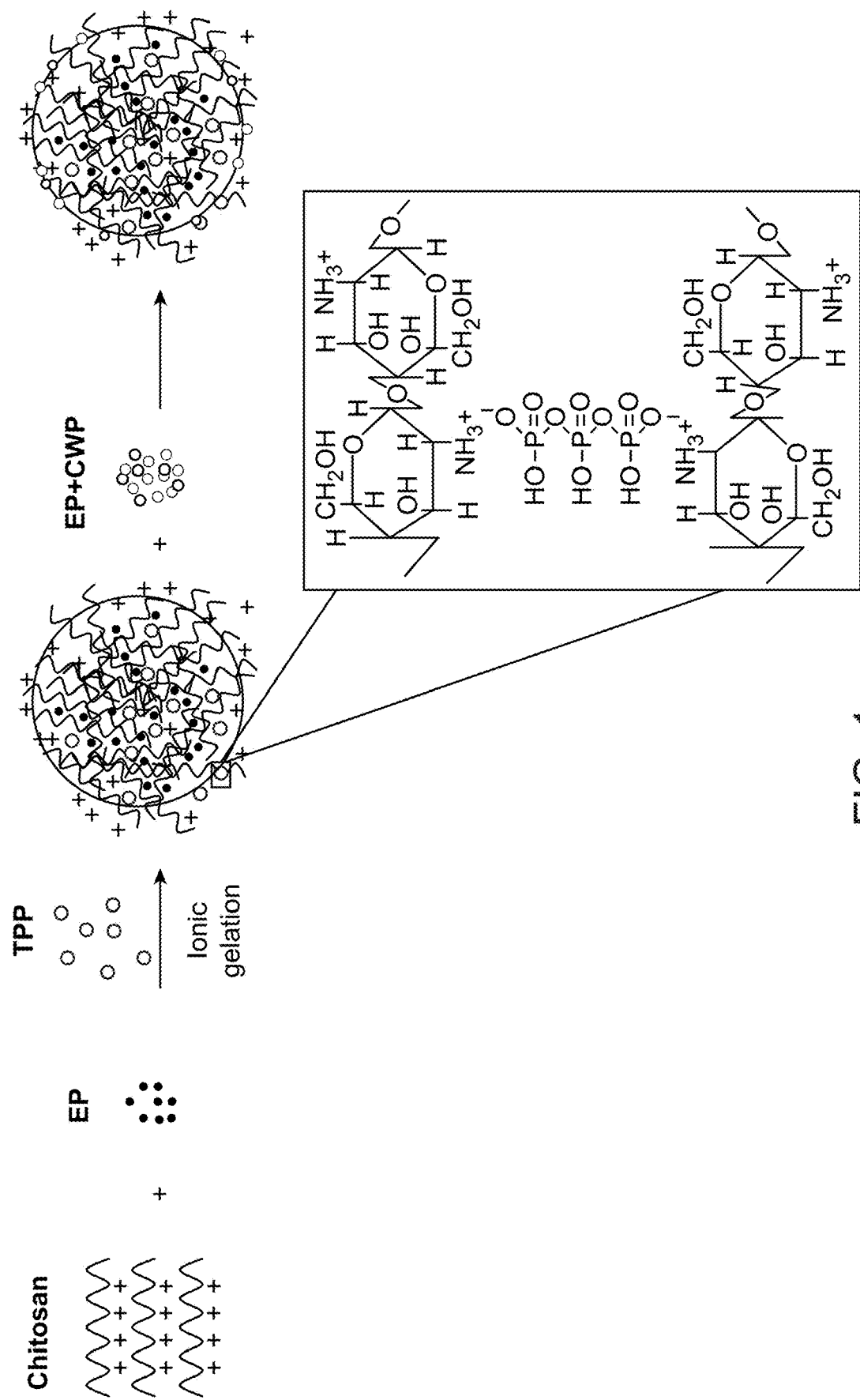
FIG. 1. Schematic for the synthesis of Ch-Np nanoparticle vaccines. TPP: Sodium tripolyphosphate. EP: Extracellular proteins. CWP: Cell wall protein.

The present disclosure relates to nanoparticles and compositions thereof for use as vaccines against *Clostridium*

*perfringens* and/or necrotic enteritis in poultry. The nanoparticles of the present invention include one or more *Clostridium perfringens* extracellular proteins entrapped within the nanoparticle. Nanoparticles are resistant to degradation in acidic microenvironment of the gut and demonstrate physiochemical properties suitable for oral deliver, such as, for example, particle size, charge, morphology, biocompatibility, and pH stability.

The nanoparticle compositions described herein may serve as vaccines for the oral delivery of one or more *Clostridium perfringens* extracellular proteins to the gastrointestinal tract of poultry, inducing mucosal and cellular immune responses to one or more *Clostridium perfringens* extracellular proteins antigens. In some aspects, nanoparticle compositions described herein provide for the targeted delivery of one or more *Clostridium perfringens* extracellular proteins antigens to ileum mucosal immune sites.

Nanoparticles may be prepared from any of a variety of biodegradable and biocompatible natural and synthetic polymers (see, for example, Dhakal and Renukaradhya, 2019, Vet Res; 50:90), including, but not limited to, chitosan nanoparticles and polyanhydride nanoparticles.

Chitosan is a polycationic, N-deacetylated derivative of chitin and composed of glucosamine (N-acetylglucosamine) polymer units (Li et al., 2015, *International Journal of Biological Macromolecules*; 75:378-387). Chitosan is biodegradable, biocompatible, non-toxic, (Zhao et al., 2014, *Int J Nanomedicine*; 9:389-402 and Zhao et al., 2014, *Int J Nanomedicine*; 9:4609-19) and resistant to degradation by gut digestive enzyme, pH changes, and temperature changes (Yata and Ghosh, 2011, *Biotechnol Lett*; 33(1):153-157). Thus, chitosan nanoparticles protect their antigen cargo until delivery to target sites (Prabaharan and Mano, 2005, *Adv Drug Deliv Rev*; 12:41-57). Chitosan structure is shown below:

Chitosan structure

Chitosan nanoparticles may be prepared, for example, by ionic gelation as described by Dhakal et al. (Dhakal et al., 2018, *Front Immunol*; 9:934), 2018). Briefly, 5 mg of either native extracellular protein (ECP) or toxoid ECP may be reconstituted in 1 ml of 1×MOPS buffer and added dropwise to 5 ml of solution of 10 mg/ml of chitosan polymer (Sigma Aldrich, St. Louis) in nano-pure water under magnetic stirring. 12.5 mg of sodium tripolyphosphate (TPP), dissolved in a 25 ml 1×PBS, may be added to the above mixture dropwise for a chitosan: TPP ratio of 4:1. to synthesize the native ECP chitosan (CN) or toxoid ECP chitosan (CT) nanoparticles. The CN and CT nanoparticles may be collected by centrifugation at 10,000×g for 30 minutes, lyophilized and stored at −80° C. until further use.

Poly(methyl vinyl ether-co-maleic anhydride), also referred to herein as polyanhydride, is well characterized, formed by the copolymerization of polyvinyl methyl ether and maleic acid. Polyanhydride nanoparticles may be synthesized by polycondensation or emulsification processes and are biodegradable, biocompatible, and safe for vaccine delivery (see, for example, Basu and Domb, 2018, *Adv Mater*; 30:e1706815; and Tones et al., 2007, *Biomaterials*; 28:108-116). They activate innate immune responses in a manner similar to lipopolysaccharides (LPS) (Petersen et al., 2011, *Biomaterials*; 32:6815-6822). Poly(methyl vinyl ether-co-maleic anhydride) structure is shown below:

Poly(methyl vinyl ether-alt-maleic anhydride) structure

Polyanhydride nanoparticles may be formulated, for example, by a solvent displacement method as described by Renu et al. (Renu et al, 2018, *International Journal of Nanomedicine*; 13:8195-8215). Briefly, 100 mg of polyanhydride (MW 216,000; Sigma-Aldrich) polymer is dissolved in 2 mL of acetone by sonication. Both ECPs and F-protein (2.5 mg each) are dispersed in 3 mL acetone and mixed with 100 mg polyanhydride solution under magnetic stirring. A total of 50 µL of SPAN® 80 (Sigma-Aldrich Co.) is added to the mixture and the solution magnetically stirred for 1 hour at room temperature. Polymer is desolvated by adding 7 mL of absolute ethanol. If desired, the nanoparticles are surface-coated with F-protein by adding 2.5 mg of F-protein in 3 mL of deionized water under magnetic stirring for 1 hour to evaporate the organic solvents. The formulated nanoparticle suspension may be cross-linked by incubation with 1,3-diaminopropane (100 µg) for 5 minutes. Nanoparticles may be collected by centrifugation at 27,000×g for 20 minutes and freeze-dried with 5% sucrose as a cryoprotectant.

In some embodiments, nanoparticles may be prepared from other related mucosal adhesive polymers, including, for example, methylglycol chitosan, glycol chitosan, high molecular weight chitosan, collagen, albumin, gelatin, alginates, cyclodextrines, dextran, agarose, hyaluronic acid, starch, cellulose, polylactic acid, polyglycolic acid, polyhydroxyl butyrate, polycaprolactone, poly doxanones, polyadipic acid, polyterphthalicacid, polysebacic acid, poly iminocarbonates, poly amino acids, polyphosphates, polyphosphonates, polyphosphazenes, poly cyanocrylates, poly urethanes, poly ortho esters, polyacetals, or combinations thereof. In some embodiments, other related cross linkers for chitosan nanoparticle formation can also be used, for example: curdlan sulfate, sodium citrate, sulfosuccinic acid, oxalic acid, glutaraldehyde, epichlorohydrin, rimethylpropane triglycidyl ether, ethylene glycol diglycidyl ether, or combinations thereof.

Nanoparticles of the compositions described herein may be any of a variety of sizes. In some aspects, nanoparticles are of a size that is effectively taken up by macrophages and other immune presenting cells through phagocytosis. See, for example, Pratten and Lloyd, 1986, *Biochim Biophys Acta*; 881(3):307-13. For example, in some aspects, nanoparticles of the compositions described herein may be about 100 nanometers (nm), about 200 nm, about 300 nm, about 400 nm, about 500 nm, about 600 nm, about 700 nm, about 800 nm, about 900 nm, about 100 nm, about 1100 nm, or any range thereof in size. For example, in some aspects, nanoparticles may be from about 100 nm to about 1,100 nm in size, about 200 nm to about 800 nm in size, about 300 nm to about 1100 nm in size, about 100 nm to about 500 nm in size, or about 150 nm to about 200 nm in size. In some aspects, nanoparticles may less than about 500 nm in size.

The nanoparticles of the present invention include one or more *Clostridium perfringens* extracellular proteins entrapped within the nanoparticle. Extracellular (ECP) proteins of *Clostridium perfringens* are immunogenic (Sengupta et al., 2010, *Infection and Immunity;* 78(9):3957-3968) and have been explored as antigens for subunit vaccines (Kulkarni et al., 2007, *Clinical and Vaccine Immunology;* 14(9):1070-1077) either in inactivated (Saleh et al., 2011, *Anaerobe;* 17(6):426-430) or in native form (Lanckriet et al., 2010, *Vaccine;* 28(36):5920-5923).

In some aspects, the one or more *Clostridium perfringens* extracellular proteins are from a *Clostridium perfringens* culture supernatant. In some aspects, the one or more *Clostridium perfringens* extracellular proteins are from the supernatant of a log phase *Clostridium perfringens* culture. Methods for the culturing of *Clostridium Perfringens* are well known and include, for example, culturing on blood agar or in thioglycolate broth at 37° C. under anaerobic conditions. In some aspects, the one or more *Clostridium perfringens* extracellular proteins are from a supernatant in which the extracellular proteins are inactivated, for example, by formaldehyde or heat treatment.

In some aspects, the one or more *Clostridium perfringens* extracellular proteins are from *Clostridium perfringens* type A, type B, type C, type D, or type E. In some aspects, the one or more *Clostridium perfringens* extracellular proteins are from *Clostridium perfringens* type A or type C. In some aspects, the one or more *Clostridium perfringens* extracellular proteins are from *Clostridium perfringens* type A. In some aspects, the one or more *Clostridium perfringens* extracellular proteins are from *Clostridium perfringens* type C.

In some aspects, the one or more *Clostridium perfringens* extracellular proteins are from a publicly available *Clostridium perfringens* strain, including, but not limited to, ATCC 13124, SM101, Str. 13, NCTC 8239, F4969, ATCC 3626, JGS1495, JGS1721, JGS1987 (Lepp et al., 2010, *PLoS ONE;* 5(5):e10795).

In some aspects, the one or more *Clostridium perfringens* extracellular proteins are from *Clostridium perfringens* strains CP1, CP4, CP5, or CP6, clinical isolates from field cases of necrotic enteritis (NE). Strains CP1 and CP4 are virulent and CP5 and CP6 are avirulent, as assessed by their abilities to cause NE (Kulkarni et al., 2006, *Clin Vaccine Immunol;* 13:1358-1362).

In some aspects, the one or more *Clostridium perfringens* extracellular proteins are from *Clostridium perfringens* strain CP6 (Thompson et al., 2006, *Vet Microbiol;* 113:25-34).

In some aspects, the one or more *Clostridium perfringens* extracellular proteins are native polypeptides, in their naturally occurring conformation.

In some aspects, the one or more *Clostridium perfringens* extracellular proteins include inactivated polypeptides, inactivated or denatured, for example, by formaldehyde or heat treatment.

The major *C. perfringens* virulence factors include genes for the production of 17 different toxins (Bokori-Brown et al., 2011, *FEBS J;* 278(23):4589-601), including, but not limited to, alpha-toxin, glyceraldehyde-3-phosphate dehydrogenase, pyruvate: ferredoxin oxidoreductase, fructose 1,6-biphosphate aldolase (Kulkarni et al., 2007, *Clinical and Vaccine Immunology;* 14(9):1070-1077). Extracellular (ECP) proteins of *C. perfringens* are immunogenic (Sengupta et al., 2010, *Infection and Immunity;* 78(9):3957-3968).

In some aspects, the one or more *Clostridium perfringens* extracellular proteins include one or more *Clostridium perfringens* toxins. In some aspects, a toxin includes, but is not limited to, alpha toxin (CPA), beta toxin (CPB), epsilon toxin (ETX), iota toxin (ITX), perfringolysin 0 (PFO), enterotoxin (CPE), beta2 toxin (CPB2), or NetB toxin. Such a toxin may be in native, active form or inactivated. An inactivated toxin may also be referred to herein as a "toxoid." In some aspects, a toxin includes an inactivated supernatant toxin.

In some aspects, a *Clostridium perfringens* extracellular protein may be isolated or purified. In some aspects a *Clostridium perfringens* extracellular protein may be isolated or purified from a *Clostridium perfringens* culture. In some aspects, a *Clostridium perfringens* extracellular protein may be produced recombinantly or synthetically.

In some aspects, a nanoparticle composition further includes a *Salmonella enteritidis* flagellar protein. In some aspects, the *Salmonella enteritidis* flagellar protein is present on the surface of the nanoparticle. In some aspects, the *Salmonella enteritidis* flagellar protein is conjugated to the surface of the nanoparticle. In some aspects, the *Salmonella enteritidis* flagellar protein entrapped within the nanoparticle. Microorganisms derived adhesive factors like flagellin decorated on the surface of the nanoparticle compositions described herein may enhance the bioadhesive nature and targeting of the nanoparticle compositions to the gastrointestinal (GI) tract and Peyer's patches (PP). Such flagellin coated nanoparticles delivered orally may adhere to the GI tract and may be actively taken up by ileum PPs immune cells.

Flagella proteins may be prepared from *Salmonella typhimurium* as described previously. See, for example, Komoriya et al., 1999, *Molecular Microbiology;* 34(4):767-779; WO 2019/035963; and Renu et al., 2018, *International Journal of Nanomedicine;* 13:8195-8215.

A nanoparticle composition or vaccine of the present invention may also include one or more compounds with adjuvant activity. Suitable compounds or compositions for this purpose include aluminum hydroxide, aluminum phosphate, aluminum oxide, plant oils, animal oils, oil-in-water or water-in-oil emulsion based on, for example a mineral oil, such as Bayol F™ or Marcol 52™, Complete Freund's adjuvant, incomplete Freund's adjuvant, or a vegetable oil such as vitamin E acetate, and saponins.

A nanoparticle composition or vaccine of the present invention may include one or more suitable pharmaceutically acceptable carriers or diluents. An immunogenic composition or vaccine of the present invention may also contain one or more stabilizers. Any suitable stabilizer can be used including carbohydrates such as sorbitol, mannitol, starch, sucrose, dextrin, or glucose; proteins such as albumin or casein; and buffers such as alkaline metal phosphate and the like.

A nanoparticle composition or vaccine of the present invention may be lyophilized.

The present invention includes a method of generating an immune response to *Clostridium perfringens* in a subject by administering a nanoparticle composition, pharmaceutical composition, or vaccine as described herein to the subject.

The present invention includes a method for protecting a bird of the order Galliformes against necrotic enteritis by administering to the bird a nanoparticle composition, pharmaceutical composition, or vaccine as described herein.

The present invention includes a method for delivery of one or more *Clostridium perfringens* extracellular proteins to the mucosal membrane of the intestinal tract of a bird of the order Galliformes, the method including the oral administration to the bird of a nanoparticle composition, pharmaceutical composition, or vaccine as described herein to the bird.

The present invention includes a method of preventing a *Clostridium perfringens* infection and/or necrotic enteritis in poultry, the method including administering a nanoparticle composition, pharmaceutical composition, or vaccine as described herein.

The present invention includes a method of controlling *Eimeria* infections and coccidiosis in poultry, the method including administering a nanoparticle composition, pharmaceutical composition, or vaccine as described herein.

The nanoparticle compositions and vaccine described herein may be administered as the active component to immunize a subject to elicit an immune response. Immunity may include the induction of a higher level of protection in a population after vaccination compared to an unvaccinated group. The immune response may, or may not, confer protective immunity. An immune response may, for example, include one or more of a cell mediated immune response, which involves the production of lymphocytes in response to exposure to the antigen and/or a humoral immune response, which involves production of plasma lymphocytes (B cells) in response to antigen exposure with subsequent antibody production. Immunization may result in the reduction, inhibition, or prevention of one or more of the symptoms of *Clostridium perfringens* infection and necrotic enteritis. Such symptoms may include one or more of death, body weight suppression, decrease in egg production, reductions in growth and feed conversion rates, mortality, damage to the intestinal epithelium, necrotic lesions in the intestinal epithelium, severe depression, decreased appetite, diarrhea, closed eyes, and ruffled feathers.

In some aspects of the methods of the present invention, administration includes injection, spraying, oral administration, or respiratory administration. In some aspects of the methods of the present invention, administration induces mucosal immunity.

In some aspects of the methods of the present invention, administration includes in ovo administration. In some aspects, in ovo administration includes administration at about 13 days, about 14 days, about 15 days, about 16 days, about 17 days, about 18 days, about 19 days, about 20 days, or any range thereof.

Compositions and vaccines of the present invention may be substantially pure. As used herein, "substantially pure" will mean material essentially free of any similar macromolecules or other biological entities that would normally be found with it in nature.

Compositions and vaccines of the present invention may be administered to birds of any of a variety of avian species that are susceptible to infection with an avian reovirus, including, but not limited to, poultry, birds of the order Galliformes, and exotic bird species. Birds of the order Galliformes include, but are not limited to, chickens, turkeys, grouse, quail, and pheasants. As used herein, poultry includes domesticated birds that are kept for the purpose of collecting their eggs or killing for their meat and/or feathers. These most typically are members of the superorder Galloanserae (fowl), especially the order Galliformes (which includes, for example, chickens, quail, turkeys, and grouse) and the family Anatidae (in order Anseriformes), commonly known as "waterfowl" (including, for example, ducks, geese, and swans). Poultry may also include other birds which are killed for their meat, such as pigeons or doves or birds considered to be game, like pheasants. Chickens include, but are not limited to, hens, roosters, broilers, roasters, layers, breeders, the offspring of breeder hens, and layers.

In some aspects, the subject includes a bird of the order Galliformes. In some aspects, the bird of the order Galliformes includes a chicken, turkey, or quail.

As used herein, the term "susceptible to" means the possibility or actuality of a detrimental response to the referenced microorganism, when compared to a non-susceptible individuals or groups, and/or one or more pathological state(s) indicative of *Clostridium perfringens* infection and/or necrotic enteritis.

The vaccine of the present invention may be administered to poultry before or after hatching. Poultry may receive a vaccine at a variety of ages. For example, broilers may be vaccinated in ovo, at one-day-old, or at 2-3 weeks of age. Laying stock or reproduction stock may be vaccinated, for example, at about 6-12 weeks of age and boosted at about 16-20 weeks of age. Such laying stock or reproduction stock may be vaccinated at about 6, at about 7, at about 8, at about 9, at about 10, at about 11, or at about 12 weeks of age. Such laying stock or reproduction stock may be boosted at about 16, at about 17, at about 18, at about 19, or at about 20 weeks of age. The offspring of such laying stock or reproduction stock may demonstrate an antibody titer to a polypeptide as described herein, which may prevent or mitigate the symptoms of a *Clostridium perfringens* infection and/or necrotic enteritis in the offspring. In ovo vaccination may take place, for example, at about 13 days, about 14 days, about 15 days, about 16 days, about 17 days, about 18 days, about 19 days, about 20 days, or at any range thereof.

Chickens may be vaccinated at any suitable age and are usually about one to three days old before first vaccination. The chickens may be vaccinated only once. Or, if two doses of vaccine are used, the first is given, for example, when the chickens are 3 days to a week old and subsequently after a further 1-10 weeks.

Multiple doses of the composition can be administered throughout the life of the chicken. As maternal immunity is a primary source of providing protection to broiler progeny, breeder chickens may be vaccinated.

A nanoparticle composition or vaccine of the present invention may be administered by any suitable known method of inoculating poultry including nasally, ophthalmically, by injection, in drinking water, in the feed, by exposure, in ovo, maternally, by respiratory inhalation, and the like. The immunogenic composition or vaccine may be administered by mass administration techniques such as by placing the vaccine in drinking water or feed, or by spraying or aerosolizing. When administered by injection, the immunogenic composition or vaccine may be administered parenterally. Parenteral administration includes, for example, administration by intravenous, subcutaneous, intramuscular, or intraperitoneal injection.

In some aspects, administration includes oral delivery. In some aspects, oral delivery includes delivery by food. In some aspects, oral delivery includes delivery by drinking water. In some aspects, oral delivery includes delivery by spraying or aerosolizing. In some aspects, oral delivery includes in ovo administration.

As used herein, "isolated" refers to material removed from its original environment (e.g., the natural environment if it is naturally occurring), and thus is altered "by the hand of man" from its natural state.

The term "and/or" means one or all of the listed elements or a combination of any two or more of the listed elements.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful and is not intended to exclude other embodiments from the scope of the invention.

The terms "comprises" and variations thereof do not have a limiting meaning where these terms appear in the description and claims.

Unless otherwise specified, "a," "an," "the," and "at least one" are used interchangeably and mean one or more than one.

Also, the recitations of numerical ranges by endpoints include all numbers subsumed within that range (e.g., 1 to 5 includes 1, 1.5, 2, 2.75, 3, 3.80, 4, 5, etc.).

For any method disclosed herein that includes discrete steps, the steps may be conducted in any feasible order. And, as appropriate, any combination of two or more steps may be conducted simultaneously.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

In several places throughout the application, guidance is provided through lists of examples, which examples can be used in various combinations. In each instance, the recited list serves only as a representative group and should not be interpreted as an exclusive list. It is to be understood that the particular examples, materials, amounts, and procedures are to be interpreted broadly in accordance with the scope and spirit of the invention as set forth herein.

All headings throughout are for the convenience of the reader and should not be used to limit the meaning of the text that follows the heading, unless so specified.

The present invention is illustrated by the following examples. It is to be understood that the particular examples, materials, amounts, and procedures are to be interpreted broadly in accordance with the scope and spirit of the invention as set forth herein.

EXAMPLES

Example 1

Characterizing and Assessing the Safety and Immunogenicity of Chitosan and Polyanhydride Nanoparticle Vaccines Loaded with *Clostridium perfringens* Antigens Cell wall-associated and extracellular proteins were extracted from exponentially growing cultures of CP6 cells following the procedure of Tavares and Sellstedt ("A simple, rapid and non-destructive procedure to extract cell wall-associated proteins from *Frankia*," *J Microbiol Methods*, 2000; 39(2):171-8). The method includes washing cells in 62.5 mM Tris-HCl (pH 6.8) buffer supplemented with 0.1% Triton X-100 as solubilizing agent. Proteins were then salted out by ammonium sulfate precipitation, followed by buffer exchange. SDS-PAGE (10%) was performed of protein preparations.

Figure 2:
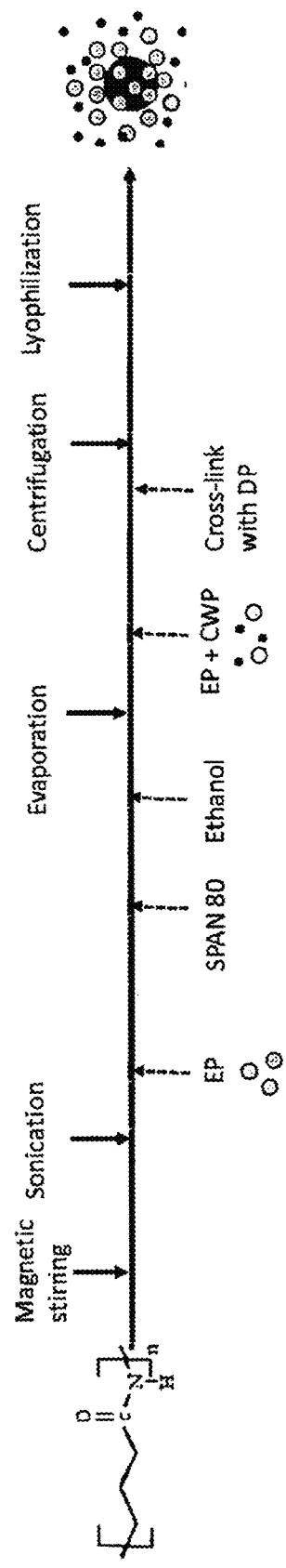
FIG. 2. Schematic for the synthesis of polyanhydride nanoparticle vaccines.
Figure 3B:
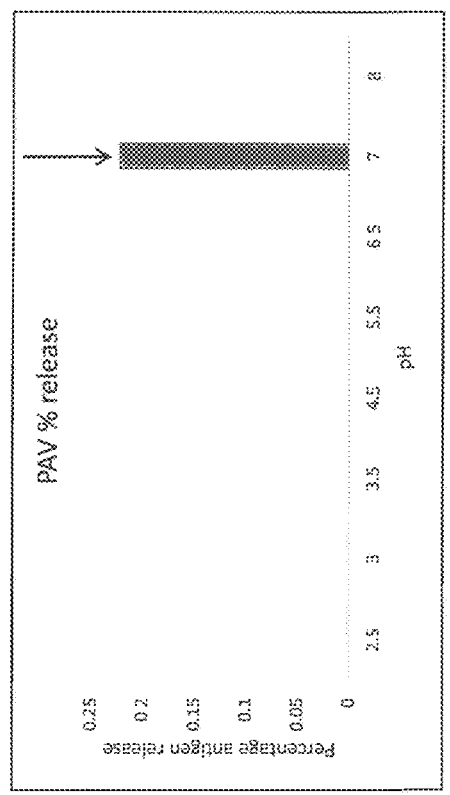
FIGS. 3A to 3C. Entrapment Efficiency, pH stability and antigen release.
Figure 3C:
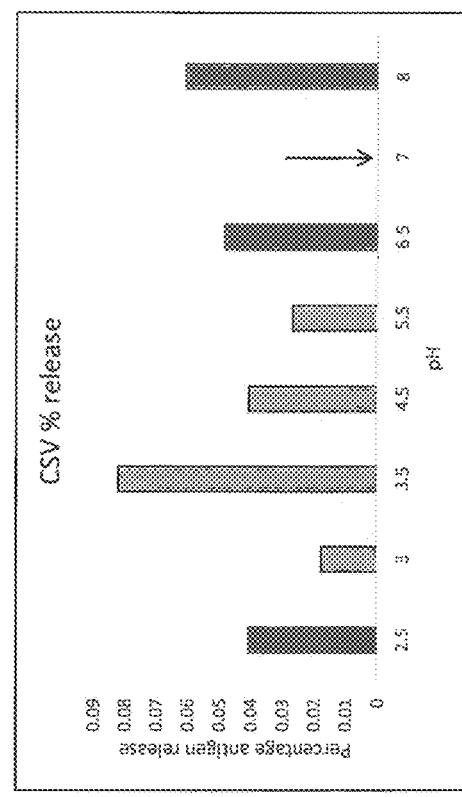
Figure 3A:
Figure 6C:
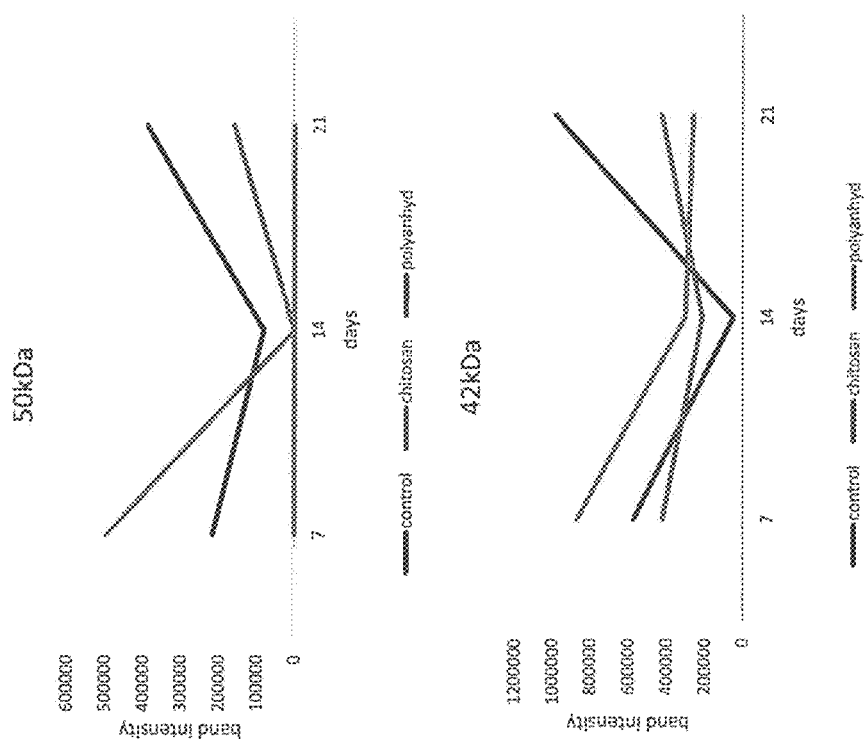
FIGS. 6A to 6D. SDS-PAGE analysis of band.
Figure 6D:
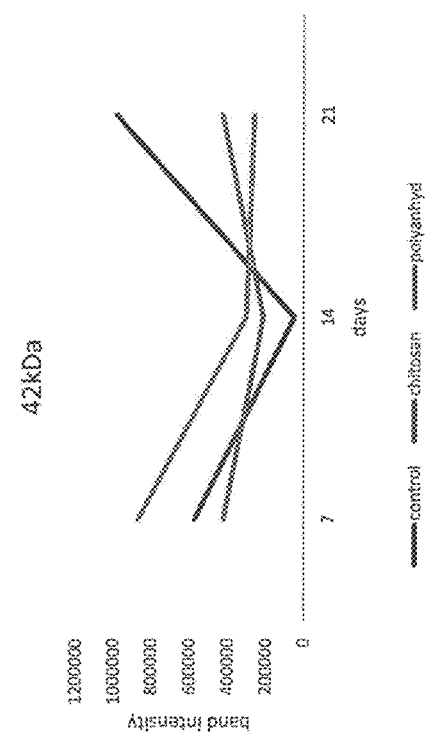
Figure 6A:
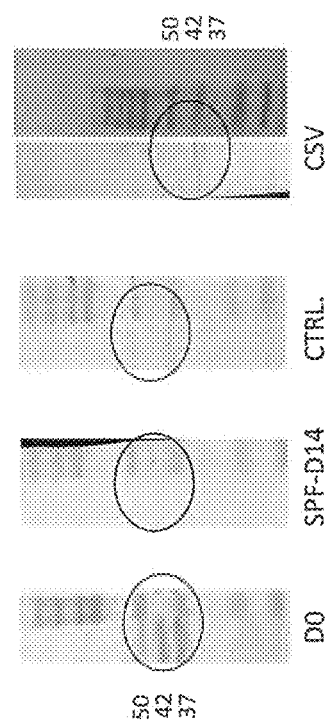
Figure 6B:
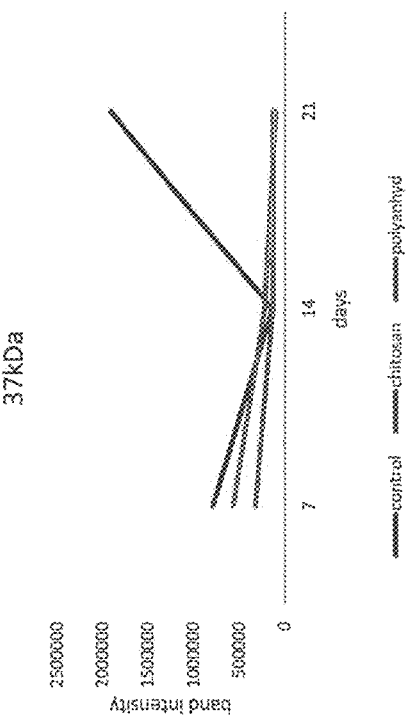

FIG. 1 shows a schematic for the design and synthesis of chitosan nanoparticle (Ch-Np) vaccines. FIG. 2 shows a schematic for the design and synthesis of polyanhydride nanoparticle vaccines. Briefly, cell FIGS. 3A to 3C show entrapment efficiency, pH stability, and antigen release. Percent antigen release was calculated as follows: EE (%)=$(Q_{associated}/Q_{initial}) \times 100$. Results for CSV=60%. Results for PAV=70%.

FIGS. 4A and 4B show results of biosafety LDH assay using LMH cells. Statistical analysis done with SAS general linear model. Alpha was set at 0.05. As an additional biosafety measure, LMH cells treated with chitosan alone, polyanhydride alone, chitosan vaccine, polyanhydride vaccine, supernatant protein, and $H_2O_2$, and untreated were viewed microscopically.

FIGS. 5A and 5B show results of safety and immunogenicity assessment. Both humoral and cellular immunity assayed. Treatments included: Ch-Np Dose 10 µg (CS10); Ch-Np Dose 50 µg (CS50); Ch-Np Dose 100 µg (CS100); P-Np Dose 10 µg (PLN10); P-Np Dose 50 µg (PLN50); P-Np Dose 100 µg (PLN100); empty chitosan nanoparticles (CHE); empty polyanhydride nanoparticles (PE); and PBS control (CTRL). FIG. 5A shows day 28 bile IgA. FIG. 5B shows day 28 serum IgG. Only Bile IgA at 28 DOA showed detectible antibody response. Statistical analysis done with SAS general linear model. Alpha was set at 0.05. Group (n=7). Male Cobbs in completely randomized design. Anova-one way (P<0.05). SDS-PAGE (10%) analysis of band intensity against 37 kDA, 50 kDa, and 42 kDa polypeptides is shown in FIG. 6A to 6D.

In summary, nanoparticle vaccine preparations are safe, have promising antigen release characteristics, can hold on to antigen over a wide pH range, and stimulate an immune response.

Example 2

In Vitro Characterization and Immunogenicity of Chitosan Nanoparticles Loaded with Native and Inactivated Extracellular Proteins from a Field Strain of *Clostridium perfringens* Associated with Necrotic Enteritis With the present example, chitosan nanoparticles were formulated with native (CN) or toxoids (CT) of extracellular proteins (ECP) of *C. perfringens* (CP), both surface-tagged with *Salmonella* flagellar proteins. In a pH stability assay, CN and CT nanoparticles released 6% and 0% of their protein at 8.0 pH. In a protein release assay, CN and CT nanoparticles released 16% and 10% of their protein respectively at 7.4 pH after 24 hours. CN and CT nanoparticles incubated at 100 μg/ml PBS with Chicken red blood cells (cRBC) released 0.7% and 0% hemoglobin, respectively. Ninety broilers were randomly assigned to treatments; sham-vaccinated (Control), CN-vaccinated (CN), and CT-vaccinated (CT). Each bird was orally gavaged with 50 μg vaccine in 0.5 ml PBS or 0.5 ml PBS only on days 0, 3, 7 and 14 post hatch. At 21 days (d) of age, chickens in the CN group had 34% higher anti-ECP IgA than control (P<0.05). At 21 d of age, the CN and CT group had 107% and 82.4% higher anti-ECP IgA (P<0.05) respectively. At 17 d of age, the CN group had 244% higher anti-flagellar IgG (P<0.05). At 10 d of age, the CN group had 14.3% higher anti-flagellar IgA than control (P<0.05). Splenic T cells from chickens in the CN and CT group stimulated with 0.05 mg/ml ECP, had 26% higher (P<0.05) and 107% higher (P<0.01) proliferation than control, respectively. Splenic T cells from chickens in the CN and CT groups stimulated with 0.1 mg/ml ECP had 46% and 63% higher proliferation than control group (P<0.05) respectively. Pooled serum from 17 d of age CN and CT-vaccinated birds neutralized toxins in 50 μg of ECP by 40% and 44% (P<0.05) respectively. Pooled serum from 28 d of age CN-vaccinated birds neutralized toxins in 50 μg of ECP by 34%.

Introduction

Necrotic enteritis (NE) is a severe *Clostridium perfringens* induced disease and is caused by type A and type C strains. Clinical NE infections occur when *C. perfringens* (CP) proliferates in the small intestine and produces exotoxins that can damage the intestinal epithelium. In recent times, clinical and subclinical NE infections have become exacerbated by the withdrawal of antibiotic growth promoters and ionophore coccidiostats. Currently there is only one commercially available CP toxoid vaccine for layer birds. This "killed" vaccine needs to be injected which can decrease production performances and the value of breast meat. Though some research to deliver the CP antigens orally have been attempted, all such research involves either attenuating a live strain (Thompson et al., 2006, *Veterinary Microbiology;* 113(1-2):25-34) or using a live vector like *salmonella* (Wilde et al., 2019). The disadvantages of applying live vaccines in poultry production for NE control has been documented (Mot et al., 2014). Therefore, developing a potent killed or subunit *C. perfringens* vaccine that can be applied orally would have potential application for the poultry industry.

The major *C. perfringens* virulence factors include genes for the production of 17 different toxins (Bokori-Brown et al., 2011, FEBS J; 278(23):4589-601). Most of the current vaccines against NE target coccidial parasites because NE has been frequently associated with coccidiosis. Earlier reports identified that vaccines designed against CP alpha-toxin, glyceraldehyde-3-phosphate dehydrogenase, pyruvate: ferredoxin oxidoreductase, fructose 1,6-biphosphate aldolase, and a hypothetical protein extracellular protein successfully induced immunity (Kulkarni et al., 2007, *Clinical and Vaccine Immunology;* 14(9):1070-1077). Extracellular (ECP) proteins of *C. perfringens* are immunogenic (Sengupta et al., 2010, *Infection and Immunity;* 78(9):3957-3968) and have been explored as antigens for subunit vaccines (Kulkarni et al., 2007, *Clinical and Vaccine Immunology;* 14(9):1070-1077) either in inactivated (Saleh et al., 2011, *Anaerobe;* 17(6):426-430) or in native form (Lanckriet et al., 2010, Vaccine; 28(36):5920-5923).

This example provides an oral vaccine based on nanocarriers that will mitigate the effect of necrotic enteritis in the poultry industry. Chitosan loaded with extracellular proteins and delivered orally to broilers will stimulate specific humoral and cell-mediated immune response.

Materials and Methods

Preparation of nanoparticle vaccine. For collection of *Clostridium Perfringens* extracellular proteins in native form, *Clostridium perfringens* CP6 (gift from Dr. C. Hofacre, Southern Poultry Research Group) was cultured on blood agar for 24 hours at 37° C. Five isolated colonies of CP6 were each inoculated into 50 ml of thioglycolate broth (Sigma Aldrich, St Louis) for 24 hours at 37° C. under anaerobic conditions. Approximately 200 ml of the stock culture of was inoculated into 2 liters of thioglycolate broth for 24 hours at 37° C. under anaerobic conditions. At 24 hours (h) of incubation the culture had an absorbance (OD600) of 0.6. The supernatant was collected after centrifugation at 11,420×g for 30 min and filtered using a 0.22 μm filter. Extracellular proteins (ECP) in the native form were precipitated from the supernatant using 106 g $(NH_4)_2SO_4$ in 200 ml of supernatant at 4° C. overnight. The native ECP was reconstituted in 40 ml of PBS, concentrated, and desalted using a 10 kDa AMICON® 8400 Ultra filter membrane (Sigma Aldrich, St. Louis) following the manufacturer's protocol. The protein concentrations in the ECP suspension was determined using Bradford reagent kit (Bio-Rad, Hercules, Calif., USA) following the manufacturer's protocol. Optical density was measured at 595 nm with a spectrophotometer (Biochek, Scarborough, Me.). The concentration of the native ECP was adjusted with 1×PBS to a final concentration of 42 mg/ml. Aliquots were lyophilized with a cryoprotectant and stored at −80° ° C. until further use.

Preparation of *Clostridium perfringens* toxoid. Preparation of ECP toxoid was carried out as described previously (Fernandes Da Costa et al., 2013, *Vaccine;* 31(37):4003-8) with modifications. 100 mg of purified native ECP was reconstituted in 100 ml 1×PBS, treated with 1 ml of formaldehyde solution (ThermoFisher scientific, Waltham, Mass.), and incubated at 37° C. for 5 days to synthesize the ECP toxoid. The reaction was stopped by adding 54.6 mg L-lysine. The toxoid was dialyzed against 1×PBS to remove excess formaldehyde, freeze dried with a lyophilizer, and stored at −80° C. until further use.

Preparation of chitosan native and toxoid ECP nanoparticles. Chitosan nanoparticles were prepared by ionic gelation as described earlier (Dhakal et al., 2018, *Front Immunol;* 9:934). 5 mg of either native ECP or toxoid ECP were reconstituted in 1 ml of 1×MOPS buffer and was added dropwise to 5 ml of solution of 10 mg/ml of chitosan polymer (Sigma Aldrich, St. Louis) in nano-pure water under magnetic stirring. 12.5 mg of sodium tripolyphosphate (TPP), dissolved in a 25 ml 1×PBS, was added to the above mixture dropwise for a chitosan: TPP ratio of 4:1. Flagella proteins were extracted from *Salmonella typhimurium* as described previously (Komoriya et al., 1999, *Molecular Microbiology;* 34(4):767-779) and reconstituted to a final concentration of 0.5 mg/ml and added to the above mixture to synthesize the native ECP chitosan (CN) or toxoid ECP chitosan (CT) nanoparticle. The CN and CT nanoparticles were collected by centrifugation at 10,000×g for 30 minutes, lyophilized and stored at −80° C. until further use.

Entrapment efficiency of ECP and flagellar proteins in the synthesized CN and CT nanoparticles. The entrapment efficiency was measured by quantifying the amount of proteins leftover in the supernatant after centrifuging the CN and CT nanoparticles at 10,000×g for 30 minutes. The protein content in 200 μl of the supernatant was measured using a Bradford reagent as described above. The entrapment efficiency was determined as follows:

Entrapment efficiency (%)=(Total protein for nanoparticle synthesis−Total protein in supernatant)/Total protein for nanoparticle synthesis×100.

In vitro cumulative protein release assay and pH stability of CN and CT nanoparticles. The stability of the synthesized CN and CT nanoparticles were measured using the in vitro protein release assay as described previously (Dhakal et al. 2018, *Front Immunol;* 9:934). 0.5 mg/ml of CN and CT nanoparticles in 3 ml of 1×PBS at 7.4 pH were incubated at 37° C. for 0, 3, 10, 17 and 24 hours. 350 μl of supernatants were collected and centrifuged at 10,000×g at 4° C. in triplicates. The protein content in 200 μl of the supernatant was analyzed using Bradford reagent as described above. The results were reported as percentage of cumulative protein released at each time point calculated according to the formula:

CPR (%)=(cumulative protein released in supernatant/0.5)×100.

The pH stability of the synthesized CN and CT nanoparticles were measured by reconstituting 0.1 mg/ml in 1×PBS at 3.0, 3.5, 4.5, 5.5, 6.5, and 8 pH. The solution was incubated at 37° C. for 3 hours and centrifuged at 10,000×g for 5 minutes at 4° C. The protein content in the supernatant was analyzed using Bradford reagent as described above. The experiment was carried out twice. The results were reported as percentage of protein released at each time point calculated according to the formula:

PR (%)=(protein released in supernatant/0.1)×100.

Effect of CN and CT nanoparticles on chicken red blood cells. The effect of CN and CT nanoparticles on chicken red blood cells (RBC) were measured by analyzing the amount of hemoglobin released from chicken RBCs using the hemolysis assay as described previously (Pan et al., 2016, *PLoS One;* 11(3):e0152074). 1 ml of blood from 3-week-old broiler chickens was collected in EDTA treated tubes. Blood was centrifuged at 750×g to collect the RBC. The RBC were washed four times with 1×PBS and reconstituted in 2 ml PBS. 10 μl of RBC suspension was incubated with 0.5 ml of PBS (negative control) or 25 g/ml or 50 g/ml or 100 g/ml CN and CT nanoparticles or pure deionized water (positive control). The solution was incubated at 37° C. with rotating agitation at 100 rpm for 3 hours and centrifuged at 750×g for 5 minutes. The absorbance values of 200 μl of the supernatant at was determined at 570 nm using a microplate reader. The experiment was carried out twice. The percentage hemolysis was calculated as follows:

([OD595 nm Absorbance (treatment−negative control)]/[OD595 nm Absorbance (positive control−negative control])×100.

Experimental animals. All animal protocols were approved by the Institutional Animal Care and Use Committee at the University of Georgia. A total of 90 one-day-old chicks (Cobb 500; Cobb hatchery, Cleveland, Ga.) were randomly distributed to one of the three treatments CTRL, CN and CT. Each treatment was replicated in six cages of five chicks per cage (n=6). Birds were vaccinated by oral gavage on day 0 (day of hatch), day 3, day 7, and day 14 with either 0.5 ml PBS (CTRL) or 50 μg CN nanoparticles in 0.5 ml PBS or 50 μg CT nanoparticles in 0.5 ml PBS. Birds were raised under standard management practices. Feed intake and body weight were measured on d 14 and d 28.

Anti-ECP- and anti-flagellar-specific IgG and IgA antibodies in serum and bile of chickens administered with CN and CT nanoparticle vaccine. Serum and bile were collected from one bird per cage (total 6 birds/treatment) at d 3, 10, 17, 21, 28 of age. The amounts of anti-ECP- and anti-flagellar-specific IgG and IgA antibodies in serum and bile were determined by ELISA as described earlier (Sengupta et al., 2010, *Infection and Immunity;* 78(9):3957-3968) with modifications. Native ECP was coated at 10 μg/ml (IgA) or 20 μg/ml (IgG) on ELISA plates (Maxisorp; Nunc). Bile was diluted to 1:200 and serum was diluted to 1:20 in PBS containing 2.5%, non-fat dry milk and 0.1% tween 20 (VWR, Radnor, Pa.). Horse radish peroxidase (HRP) conjugated polyclonal goat anti-chicken IgG (Bethyl, Montgomery, Tex.) at 1:20,000 dilution or HRP-conjugated polyclonal goat anti-chicken IgA (SouthernBiotech, Birmingham, Ala.) at 1:10,000 was used as a secondary antibody. Optical density was measured as absorbance at 450 nm using a spectrophotometer (Winooski, Vt., USA) and values are reported as OD450.

Ex vivo recall response of splenic T cells of chickens administered with CN and CT nanoparticle vaccine. Spleen samples were collected from one bird/cage on d 17 and d 21 post hatch. Splenic lymphocytes were collected as described earlier (Shanmugasundaram et al., 2018, *Poultry Science;* 94:1828-1835). Approximately $5 \times 10^5$ lymphocytes were plated in triplicates per sample in 100 μl of RPMI-1640 (Sigma Aldrich, St. Louis) supplemented with 10% fetal bovine serum and 1% penicillin and streptomycin. Zero (PBS) or 0.05 mg/ml or 0.1 mg/ml or 0.25 mg/ml or 0.5 mg/ml native ECP was added to each well and incubated for 5 d at 37° C. in the presence of 5% $CO_2$. Lymphocyte proliferation was measured using the MTT ([3-(4,5-dimethylthiazol-2-yl)-2,5-diphenyltetrazolium bromide])) assay as described earlier (Wang et al., 2012). Optical density was measured at OD570 using a spectrophotometer as described above and values are reported as OD570.

Effect of serum antibodies from chickens administered with CN and CT nanoparticle vaccine on ECP neutralization. The effect of serum antibodies on ECP neutralization was analyzed as described previously (Eby et al., 2017, *Clin Vaccine Immunol;* 24(1):e00370-16) with modifications. Serum and bile were collected at d 17, d 21 and d 28 post hatch from four birds/treatment and diluted to 1:20 and 1:200, respectively in RPMI-1640 supplemented with 10% fetal bovine serum and 1% Penicillin and Streptomycin. Splenocytes were collected as described earlier (Dhakal et al., 2018, *Front Immunol;* 9:934). Approximately $10^6$ splenocytes were seeded in 96 well plates in triplicates per sample in 100 μl RPMI containing 10% fetal bovine serum and 1% Penicillin and Streptomycin. The cells were incubated at 37° C. and 5% $CO_2$ for 6 hours (hr). For each well of a neutralization plate, 75 μl of 1:20 serum or 1:200 bile was incubated with 75 μl of either 0 (toxin negative control), 0.001 mg/ml or 0.5 mg/ml or 1 mg/ml native ECP for 1 hr at 37° C. with rotating agitation to neutralize toxins. Three sets of wells with media and toxin only were maintained as toxin positive control). 100 μl of the neutralizing solution was added to splenocytes and further incubated for 4 days (d) at 37° C. and 5% $CO_2$. Splenocyte proliferation was measured using the MTT assay as described above. Optical density was measured at OD570 using a spectrophotometer as described above. The percentage toxin neutralization was determined as follows:

[OD$_{570}$ nm Absorbance (treatment−toxin positive control)/OD$_{570}$ nm Absorbance (negative control−toxin positive control)]×100.

SDS-PAGE and western immunoblotting. Approximately 67 μg native ECP and flagellar proteins were separated on a 10% SDS-PAGE gel at 100V for 1 hour 30 minutes and stained with Coomassie R250 stain as described earlier (Zhao et al., 2012, *PLoS ONE*; 7(12):1-11). The PVDF membrane was incubated with 1:50 dilution of pooled sera from all 6 birds per treatment at day 21 post hatch. An HRP-conjugated polyclonal goat anti-chicken IgA (SouthernBiotech, Birmingham, Ala.) at 1:10,000 was used as a secondary antibody. The bands were visualized using an imager (Biorad, Hercules, Calif.) and analyzed using Image Lab™ software (v. 6.0.1).

Statistical analysis. All statistical analyses were carried out with SAS program (version 9.4, SAS Institute Inc., Cary, N.C., USA). Analysis of performance, humoral and recall response was carried out using one-way analysis of variance (ANOVA) and pre-planned orthogonal contrasts. Analysis of toxin neutralization was carried out with Kruskal Wallis Chi square test on Wilcoxon's scores of rank sums. Significance was determined at P<0.05 and/or at P<0.01.

Results

Entrapment efficiency of ECP and flagellar proteins in the synthesized CN and CT nanoparticles. The entrapment efficiency for both CN and CT was 70%.

Figure 7A:
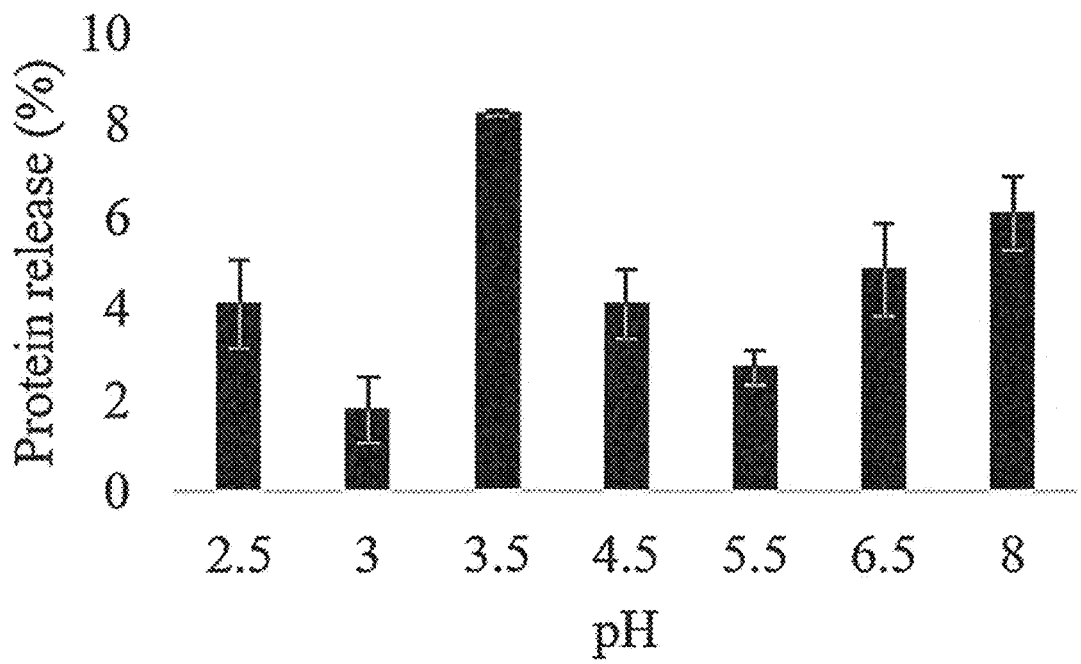
FIGS. 7A and 7B. In vitro cumulative protein release assay and pH stability of CN and CT nanoparticles. Chitosan-native (CN) and chitosan-toxoid (CT) nanoparticles were incubated in PBS and the cumulative antigen release was measured at indicated time points using the Bradford assay (FIG. 7A). Chitosan-native (CN) and chitosan-toxoid (CT) nanoparticles were incubated in solutions of different pH for 3 three hours and the percentage of total protein released was measured using the Bradford assay (FIG. 7B). Means+SD. n=2.
Figure 7B:
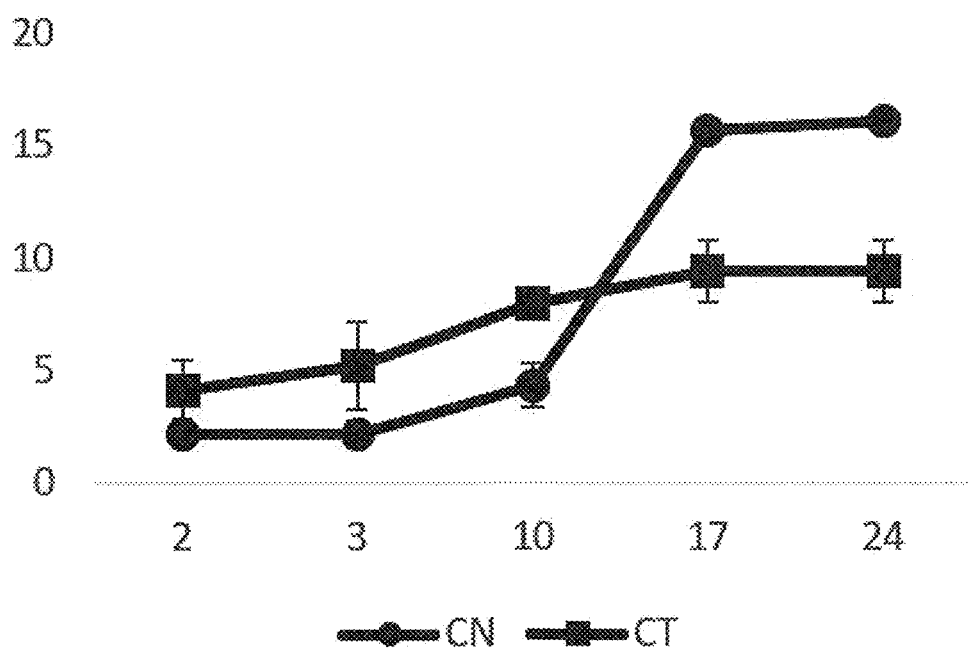

FIGS. 7A and 7B show the results of in vitro cumulative protein release assay and pH stability of CN and CT nanoparticles. Chitosan-native (CN) and chitosan-toxoid (CT) nanoparticles were incubated in PBS and the cumulative antigen release was measured at indicated time points using the Bradford assay (FIG. 7A). Chitosan-native (CN) and chitosan-toxoid (CT) nanoparticles were incubated in solutions of different pH for three hours and the percentage of total protein released was measured using the Bradford assay (FIG. 7B).

In vitro cumulative antigen release assay and pH stability of CN and CT nanoparticles. CN nanoparticles released 4% and 6% of antigen at 2.5 pH and 8.0 pH respectively while CT nanoparticles did not release measurable antigens at any of the pH assayed.

CN nanoparticles released 2% of its antigen while CT nanoparticles released 4% of its antigen during the first two hours of incubation (FIG. 7A). At 24 h of incubation, CN nanoparticles released had released 16% of antigen while CT had released 10% of its antigen.

Effect of CN and CT nanoparticles on chicken red blood cells. Chicken RBC (cRBC) incubated with 25 μg/ml, 50 μg/ml and 100 μg/ml of CN nanoparticles had 1.4%, 1% and 0.7% hemolysis, respectively. Chicken RBC incubated with 50 μg/ml and 100 μg/ml of CT nanoparticles had 0% hemolysis. This is shown in Table 1 below.

TABLE 1

| | RBC Hemolysis (%) | | |
|---|---|---|---|
| Treatment | 25 μg/ml | 50 μg/ml | 100 μg/ml |
| CN | 1.4 ± 0.002 | 1.0 ± 0.0007 | 0.7 ± 0.0006 |
| CT | 0.021 ± 0.03 | 0.0 ± 0.0 | 0.0 ± 0.0 |

Effect of CN and CT nanoparticles on chicken red blood cells. Chitosan-native (CN) and chitosan-toxoid (CT) nanoparticles were synthesized by entrapping *Clostridium perfringens* extracellular proteins and flagellar proteins. Mean ± standard deviation. (n = 2).

In vivo study—Production performance of chickens administered with CN and CT nanoparticles. CN and CT nanoparticle administration did not significantly affect the body weight gain and feed conversion ratio at d 14 and 28 of age. This is shown in Table 2 below.

TABLE 2

| | 0 to 14 | | 14 to 28 | | % |
|---|---|---|---|---|---|
| Treatment | BWG (g) | FCR | BWG (g) | FCR | mortality |
| Control | 340 | 1.80 | 1410 | 1.9 | 2/30 |
| CN | 350 | 1.55 | 1440 | 1.7 | 0/30 |
| CT | 340 | 1.71 | 1485 | 1.6 | 0/30 |
| SEM | 13 | 0.14 | 76 | 0.2 | |
| P-value | 0.80 | 0.45 | 0.82 | 0.44 | 0.13 |

The performance of broilers birds vaccinated with CN and CT vaccine. Chitosan-native (CN) and chitosan-toxoid (CT) nanoparticles were synthesized by entrapping *Clostridium perfringens* extracellular proteins and flagellar proteins. Day old chicks were orally gavaged with either 0.5 ml PBS (Control) or 50 μg CN or 50 μg CT nanoparticles in 0.5 ml PBS on 0 (day of hatch), 3, 7, and 14 d of age. Body weight gain (BWG) and feed conversion ratio (FCR) were measured on d 14 and 28. Mean of 6 replicates (n = 6).

Figure 8A:
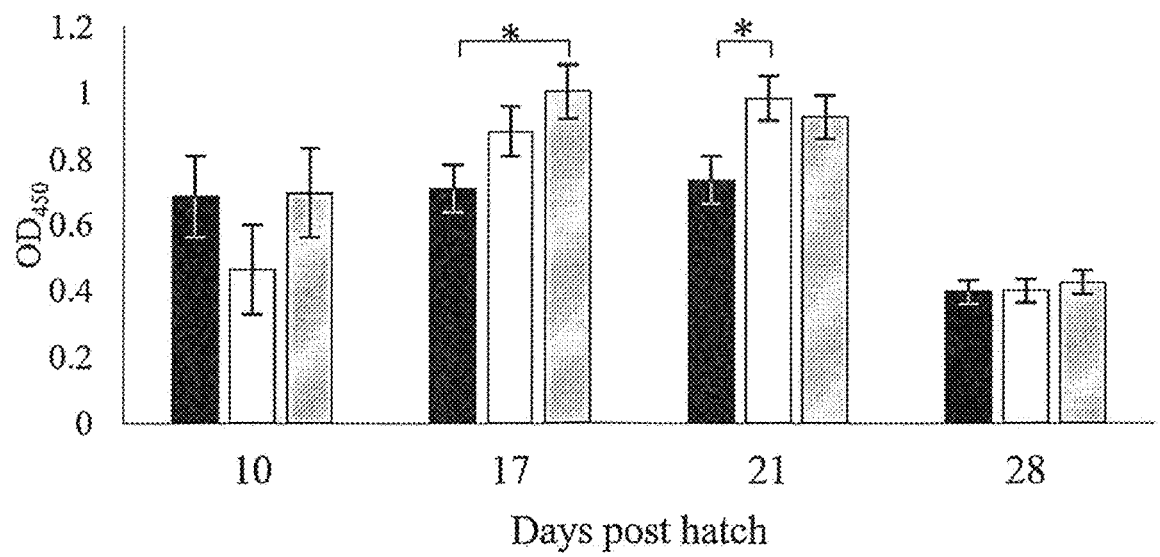
FIGS. 8A to 8D. Anti-ECP- and anti-flagellar-specific IgG and IgA antibodies in serum and bile. Chitosan-native (CN) and chitosan-toxoid (CT) nanoparticles were synthesized by entrapping *Clostridium perfringens* extracellular proteins (ECP) and flagellar proteins. Day old chicks were orally gavaged with either 0.5 ml PBS (Control) or 50 μg CN or 50 μg CT nanoparticles in 0.5 ml PBS on 0 (day of hatch), 3, 7, and 14 days (d) of age. On d10, d17, d21 and d28 of age, anti-ECP IgA (FIG. 8A), anti-ECP IgG (FIG. 8B), anti-flagellar IgA (FIG. 8C) and anti-flagellar IgG (FIG. 8D) amounts were analyzed by ELISA and values reported as Optical density (OD) values. Mean+SEM. n=6 replicates. P<0.05.
Figure 8B:
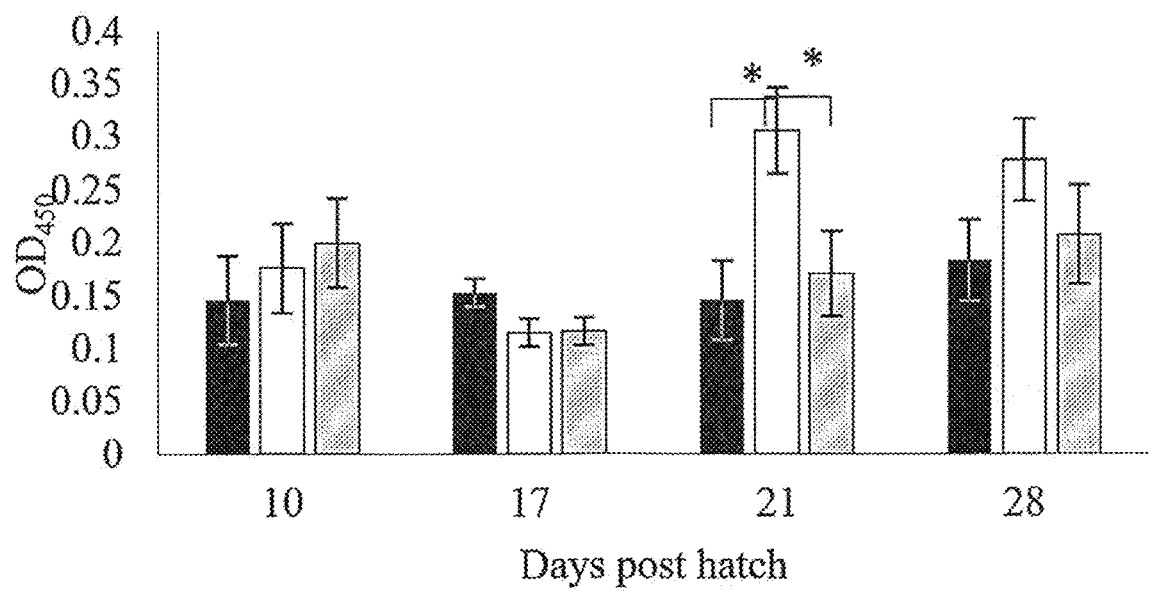
Figure 8C:
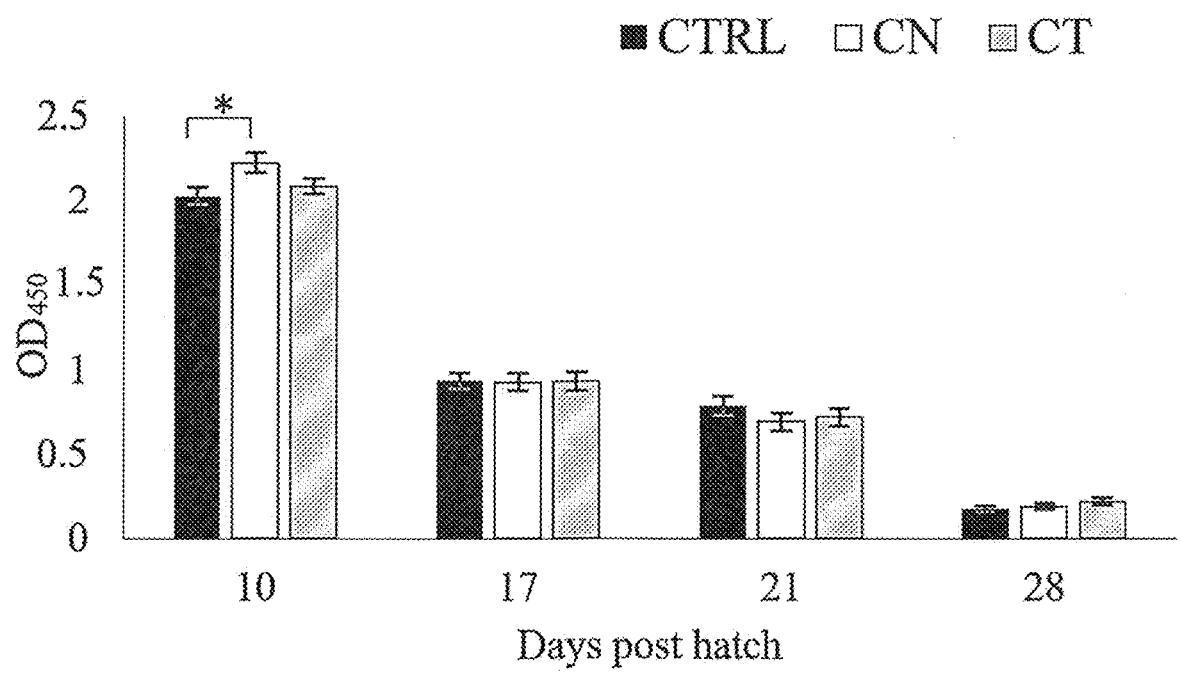
Figure 8D:
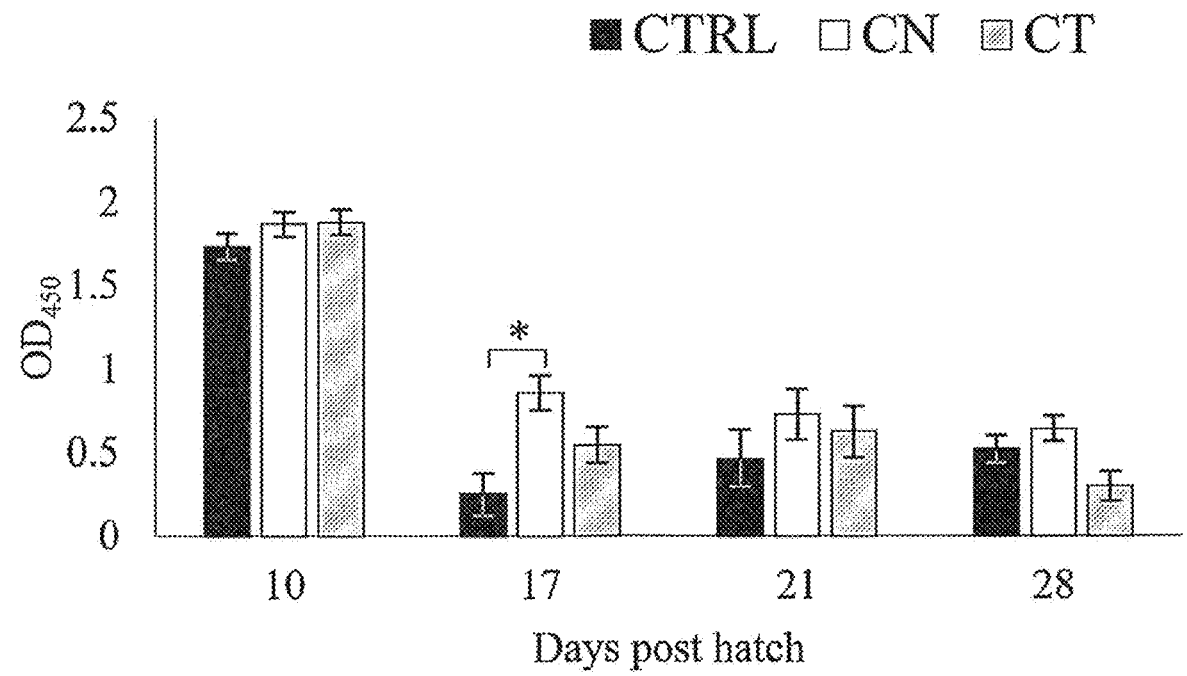

Anti-ECP- and anti-flagellar-specific IgG and IgA antibodies in serum and bile of chickens administered with CN and CT nanoparticle vaccine. At 21 d of age, chickens in the CN group had 34% higher anti-ECP IgA than that in the control group (FIG. 8A). At 28 d of age, chickens in the CN and CT group had comparable anti-ECP IgA to that in the control group. At 21 d of age, chickens in the CN and CT group had 107% and 82.4% higher anti-ECP IgG than that in the control group, respectively (FIG. 8B). At 28 d of age, chickens in the CN and CT group had comparable anti-ECP IgG to that in the control group. At 10 d of age, chickens in the CN group had 14.3% higher anti-flagellar IgA than that in the control group (FIG. 8C). At 17, 21, and 28 d of age, chickens in the CN and CT group had comparable anti-flagellar IgA to that in the control group. At 17 d of age, chickens in the CN group had 244% higher anti-flagellar IgG than that in the control group (FIG. 8D). At 10, 21, and 28 d of age, chickens in the CN and CT group had comparable anti-flagellar IgA to that in the control group.

Figure 9:
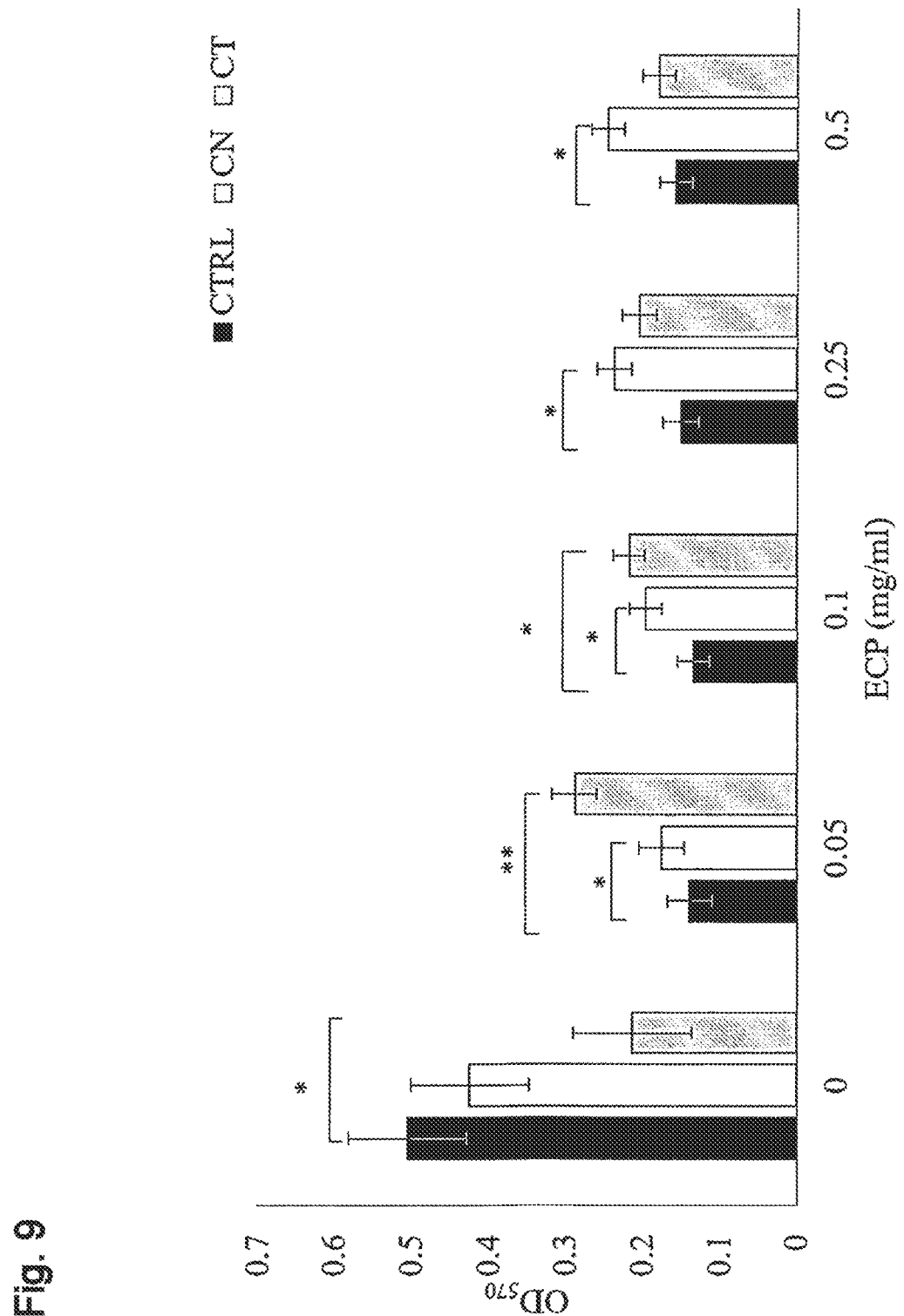
FIG. 9. Ex vivo recall response of splenic T cells of chickens administered with CN and CT nanoparticle vaccine. Chitosan-native (CN) and chitosan-toxoid (CT) nanoparticles were synthesized by entrapping *Clostridium perfringens* extracellular proteins (ECP) and flagellar proteins. Day old chicks were orally gavaged with either 0.5 ml PBS (Control) or 50 μg CN or 50 μg CT nanoparticles in 0.5 ml PBS on 0 (day of hatch), 3, 7, and 14 days (d) of age. Splenic lymphocytes were collected on d17. Lymphocytes were stimulated with 0, 0.05, 0.1, 0.25 or 0.5 mg/ml ECP for 5 d. Lymphocyte proliferation was measured using MTT assay and values reported as Optical Density (OD) values. Mean+SEM. n=6 replicates. P<0.05.

Ex vivo recall response of splenic T cells of chickens administered with CN and CT nanoparticle vaccine. Splenic T cells obtained from chickens in the CN and CT group and stimulated with 0.05 mg/ml ECP had 26% and 107% higher proliferation than that in the control group, respectively (FIG. 9). Splenic T cells from chickens in the CN and CT group stimulated with 0.1 mg/ml ECP had 46% and 63% higher proliferation than that in the control group, respectively.

Figure 10:
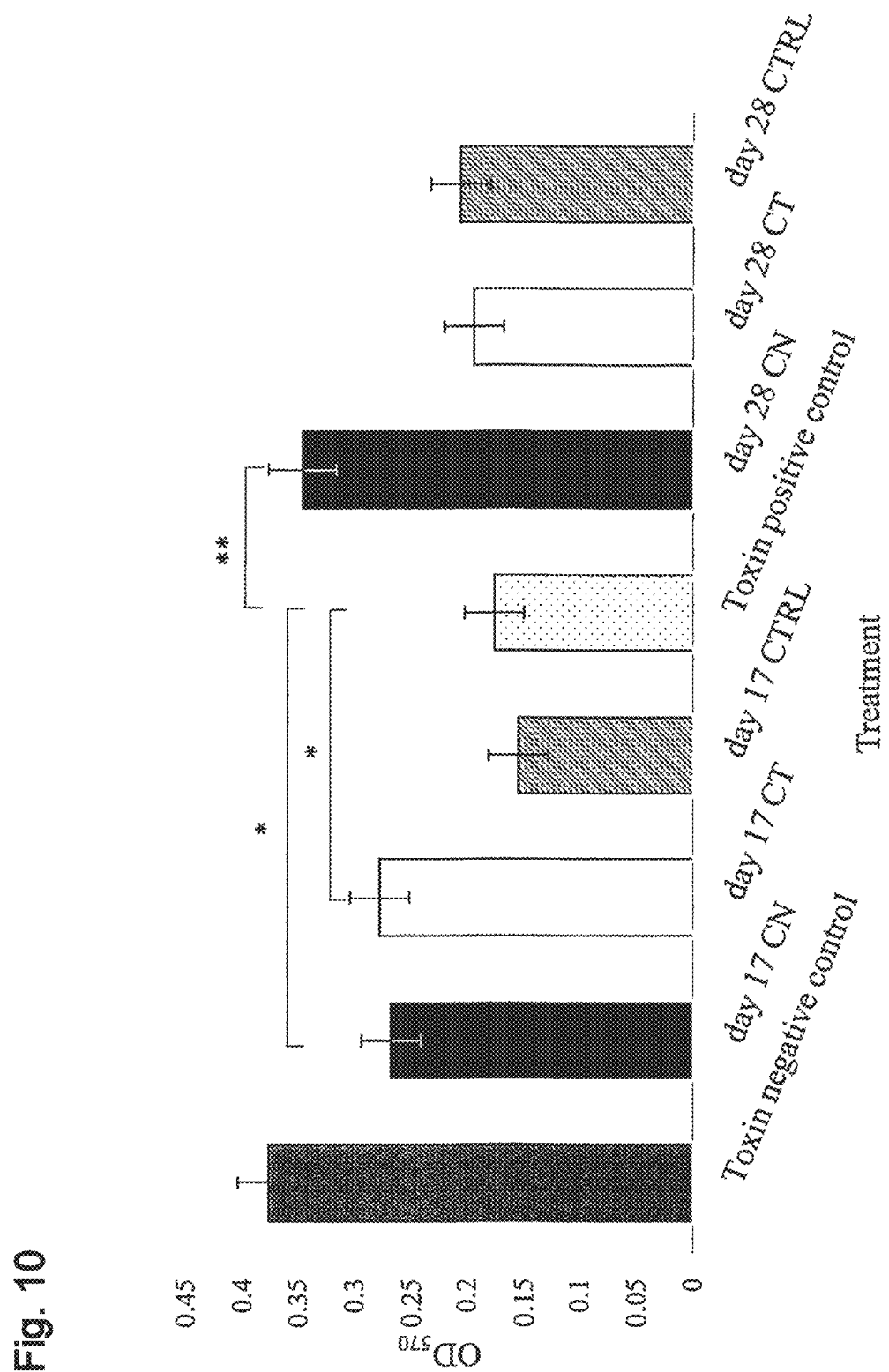
FIG. 10. Effect of serum antibodies from chickens administered with CN and CT nanoparticle vaccine on ECP neutralization. Chitosan-native (CN) and chitosan-toxoid (CT) nanoparticles were synthesized by entrapping *Clostridium perfringens* extracellular proteins (ECP) and flagellar proteins. Day old chicks were orally gavaged with either 0.5 ml PBS (Control) or 50 μg CN or 50 μg CT nanoparticles in 0.5 ml PBS on 0 (day of hatch), 3, 7, and 14 days (d) of age. Serum and bile were collected at 17, 21 and 28 days of age and incubated with 1 mg/ml native ECP to neutralize ECP. Splenocytes from normal birds were incubated with the above neutralizing solution for 4 d Splenocyte p proliferation was measured using MTT assay and values reported as Optical Density (OD) values. Mean+SEM. n=6 replicates. P<0.05.

Effect of serum antibodies from chickens administered with CN and CT nanoparticle vaccine on ECP neutralization. Pooled serum from CN and CT-vaccinated birds neutralized toxins in 50 μg of ECP at 17 days post hatch by approximately 40% and 44% respectively (P<0.05). As shown in FIG. 10, only pooled serum from CN-vaccinated birds neutralized toxins in 50 μg ECP at 28 dph, doing so by 34% (P<0.05).

Figure 11A:
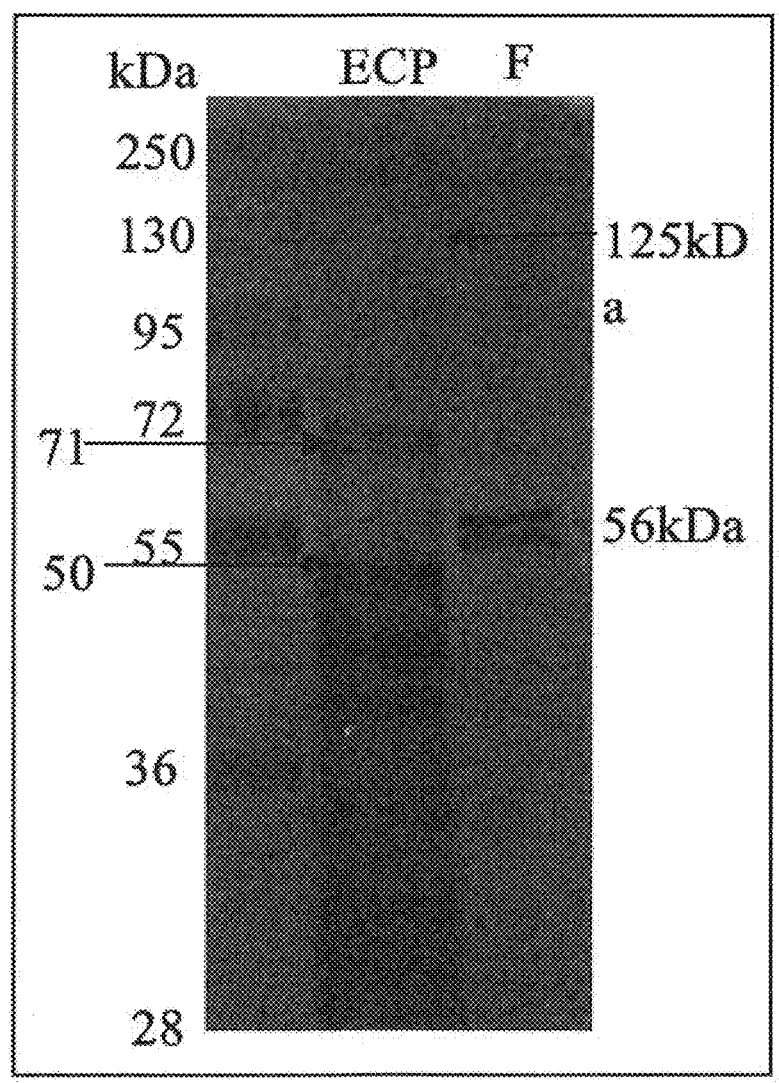
FIGS. 11A to 11D. SDS-PAGE and Western immunoblot. Extracellular proteins (ECP) were extracted from *Clostridium perfringens* and flagellar proteins were extracted from *Salmonella enteritidis* and separated on a gel and stained with Coomassie Blue (FIG. 11A). Chitosan-native (CN) and chitosan-toxoid (CT) nanoparticles were synthesized by entrapping ECP and flagellar proteins. Day old chicks were orally gavaged with either 0.5 ml PBS (Control) or 50 μg CN or 50 μg CT nanoparticles in 0.5 ml PBS on 0 (day of hatch), 3, 7, and 14 days (d) of age. At day 21 post hatch, serum was collected from birds in control (FIG. 11B), CN (FIG. 11C) and CT (FIG. 11D) and used as a primary antibody in the western blot of ECP and flagellar proteins.
Figure 11B:
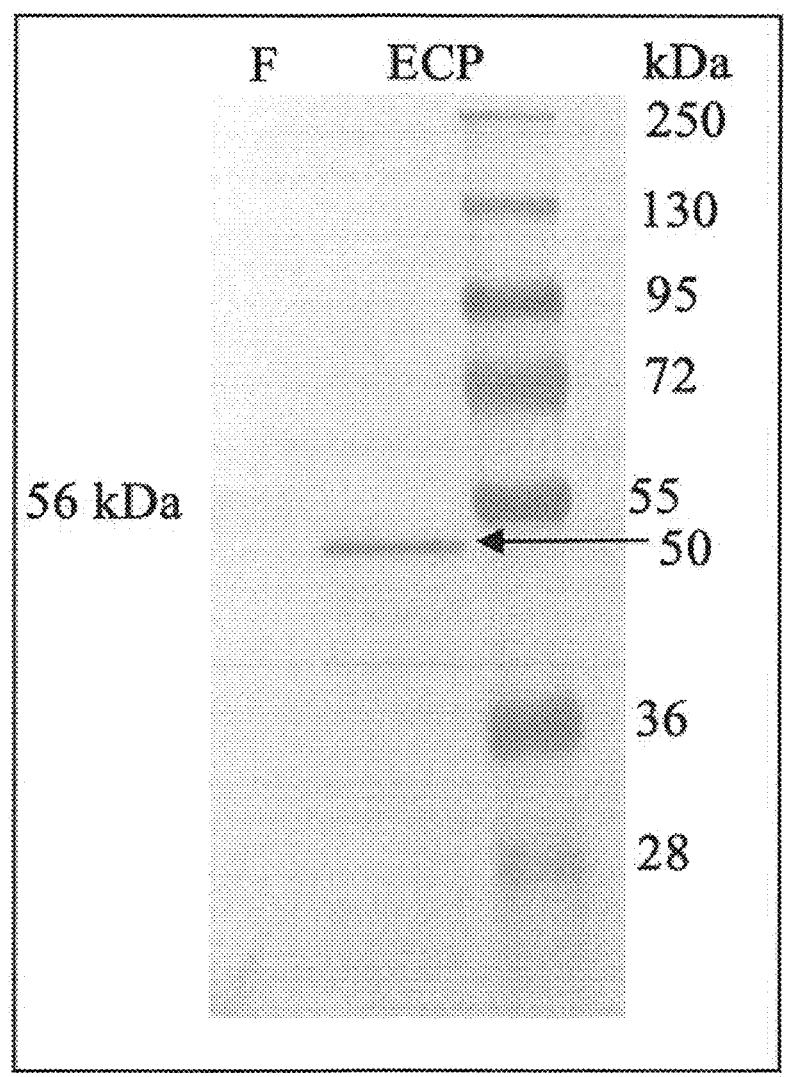
Figure 11C:
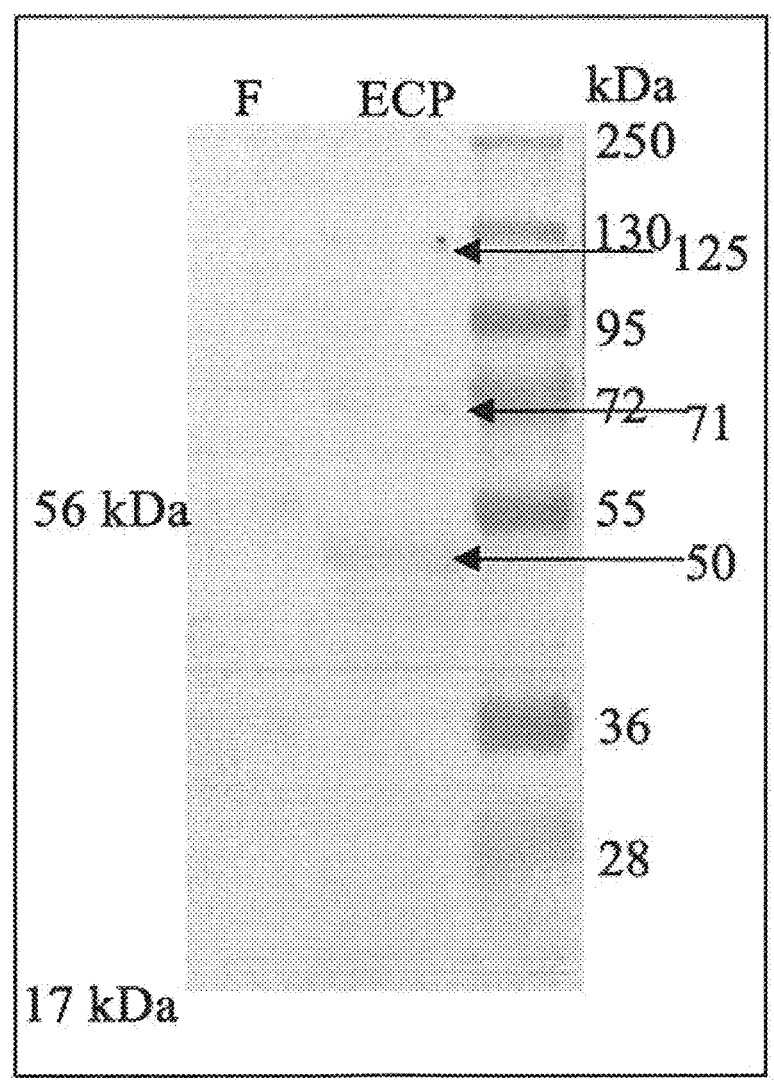
Figure 11D:
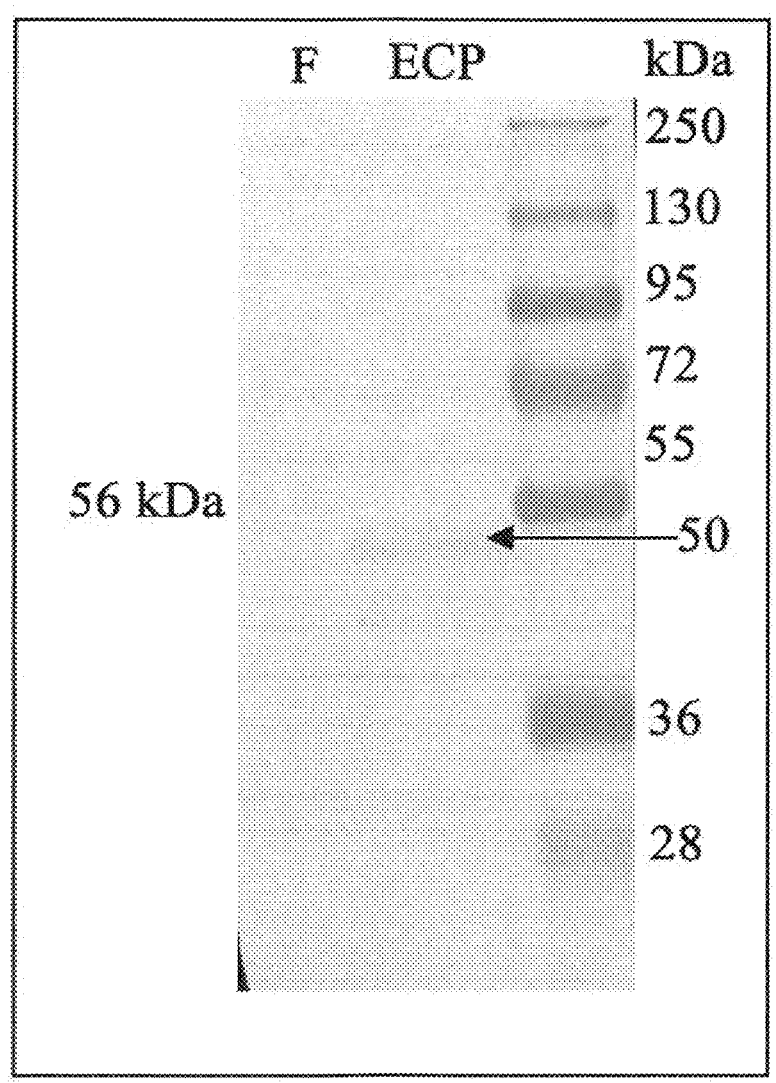

SDS-PAGE and Western Immunoblot. Extracellular proteins (ECP) were extracted from *Clostridium perfringens* and flagellar proteins were extracted from *Salmonella enteritidis* and separated on a gel and stained with Coomassie Blue (FIG. 11A). Chitosan-native (CN) and chitosan-toxoid (CT) nanoparticles were synthesized by entrapping ECP and flagellar proteins. Day old chicks were orally gavaged with either 0.5 ml PBS (Control) or 50 μg CN or 50 μg CT nanoparticles in 0.5 ml PBS on 0 (day of hatch), 3, 7, and 14 days (d) of age. At day 21 post hatch, serum was collected from birds in control (FIG. 11B), CN (FIG. 11C) and CT (FIG. 11D) and used as a primary antibody in the western blot of ECP and flagellar proteins.

Serum from birds vaccinated with CN nanoparticle vaccine identified a 125 kDa, 71 kDa and 50 kDa protein in the ECP fraction of *C. perfringens* antigens.

Discussion

This example identified the physicochemical properties, safety and immunogenicity of chitosan nanoparticles loaded with *C. perfringens* extracellular proteins and *S. typhimurium* flagella proteins. The entrapment efficiencies of CN and CT nanoparticles were 70%. CN and CT nanoparticles released 16% and 10% of their cargo respectively, after 24 hours incubation at 7.4 pH. Earlier studies reported that Chitosan nanoparticles loaded with Newcastle disease virus F protein released 30% protein (Zhao et al., 2012, *PLoS ONE*; 7(12):1-11) and chitosan nanoparticles loaded with killed swine influenza antigen released 10% protein (Dhakal et al., 2018, *Front Immunol*; 9:934) after 24 hours. A chitosan:TPP ratio of 4:1 was used for this study. Hou et al., (2012) demonstrated that as the chitosan:TPP ratio increases, protein loading efficiency decreases and protein release from the nanoparticle increases (Hou et al., 2012). CN and CT nanoparticle were stable and released less than 8% of their antigen cargo at pH between 2.5 and 8. The pH of the avian gastrointestinal tract typically ranges from 3 in the gizzard to 7 in the ceca (Sadeghi et al., 2016, *Comparative Clinical Pathology*; 25(2):257-263).

Vaccine antigen had a prominent band at 56 kDa for flagella and 121 kDa, 71 kDa and 50 kDa for ECP. Earlier reports identified flagellar protein size as 53 kDa (Sophie, et al., 2006) and hence the antigen used in the study is very likely to be flagellar protein. Kulkarni et al. (2006) identified a 33 kDa, 37 kDa and 52 kDa immunoreactive proteins in the serum of broilers that were orally gavaged with CP4.

CN and CT nanoparticles released less than 2% and less than 1% hemoglobin from cRBCs indicating that the CN and CT nanoparticles do not have an adverse effect on cells. Although toxins can be made safe for vaccination by coating in nanoparticle (Huff et al., 2005). Chitosan nanoparticles have been demonstrated to be safe in chicken embryo kidney (CEK) cells (Zhao et al., 2012, *PLoS ONE*; 7(12):1-11). In vivo, CN and CT nanoparticles vaccination did not significantly affect BWG, FCR and mortality. Earlier studies reported that chickens gavaged with chitosan nanoparticles did not have any effect on mortality (Zhao et al., 2012, *PLoS ONE*; 7(12):1-11; and Dhakal et al., 2018, *Front Immunol*; 9:934).

The oral vaccination of chickens with the CN and CT nanoparticles induced anti-ECP or anti-flagella IgG or IgA. Flagella antigens were included for their adjuvant properties in this study. Earlier study also included flagellar protein as an adjuvant (Gupta, et al., 2014). There was significant induction of IgG and IgA in the CN vaccinated group at day 21 post hatch. The 21-day time point is critical because maternal antibodies against *C. perfringens* wanes at 2 to 3 weeks post hatch leading to clostridial enteritis in chickens (Shojadoost et al., 2012, *Veterinary Research*; 43(1):74). Subcutaneous vaccination of chickens with *clostridium* proteins induced antigen specific IgG in serum at 20 days post hatch and decreased intestinal lesions (Tang et al., 2012). Oral vaccination of chickens with live *C. perfringens* induced serum and mucosal antibody responses at day 22 post hatch and decreased intestinal lesions (Mishra & Smyth, 2017).

This example determined that antibodies in the serum of chickens vaccinated with CN and CT nanoparticles partially neutralized the cytotoxicity of ECP on splenocytes. Kulkarni et al. (2006) identified that antibodies in serum and intestinal washes of birds vaccinated with alpha-toxin reduces the lecithinase activity of alpha-toxin on 5% egg yolk agar (Kulkarni et al., 2006). Serum from vaccinated birds were analyzed to identify if the antibodies in the serum of vaccinated birds immunoreacted with the antigen that was used to synthesize the nanoparticle vaccine. Serum from birds vaccinated with the CN nanoparticle vaccine immunoreacted with three proteins in ECP while that from CT nanoparticle group immunoreacted with one protein. Birds vaccinated with CN nanoparticle vaccine had higher serum IgG than that in the CT vaccinated group at day 21 post hatch. Similar to this study, Kulkarni et al. (Kilkarni et al., 2006, *Clin Vaccine Immunol*; 13(12):1358-62) demonstrated that serum from chickens immunized with *C. perfringens* recognize antigens in the vaccine.

Splenic lymphocytes from chickens that were vaccinated with CN and CT nanoparticles had a higher recall response than controls. A similar study demonstrated that splenic lymphocytes of chickens vaccinated with chitosan nanoparticles loaded with antigen leads to a higher recall response (Zhao et al., 2012, *PLoS ONE*; 7(12):1-11). Fasina and Lillehoj (Fasina and Lillehoj, 2019, *Poult Sci*; 98(1):188-198) showed that T cells are involved in the immune responses of chickens to *Clostridium enteritis*.

CONCLUSION

This example determined the physicochemical characteristics and immunogenicity of chitosan nanoparticles loaded with extracellular proteins of *C. perfringens* and *Salmonella* flagella proteins. Briefly, chitosan nanoparticle vaccines were formulated with native toxins (CN) or toxoids (CT) from extracellular proteins (ECP) of *C. perfringens*. Both the vaccines were surface tagged with *Salmonella* flagellar proteins. CN vaccines incubated at 3.5 pH and 41° C. for 3.5 hours released 8.2% of its cargo. The CN and CT vaccines incubated at 7.4 pH and 41° C. for 10 days released a cumulative total of 10% and 20% of their antigens, respectively. The CN and CT vaccines incubated at 37° C. for 3.5 hours released 17% and 8% hemoglobin respectively from chicken red blood cells. In an in vivo study, ninety broilers were randomly assigned to three treatments; sham-vaccinated (CTRL), CN-vaccinated (CN), and CT-vaccinated (CT) in six replicates. Each bird was orally gavaged with 50 µg vaccine in 0.5 ml PBS or 0.5 ml PBS only on 0-, 3-, 7- and 14-days post hatch. On 10-, 17-, 21- and 28-days post hatch, sera and bile were analyzed for anti-ECP and anti-flagella IgY and IgA. Bile Anti-ECP IgA was significantly higher in CN and CT groups than that in the CTRL group (P<0.05) at 21- and 17-days post hatch, respectively. Bile anti-flagella IgA was significantly higher in the CN group than CTRL group at 10 days post hatch. Serum anti-ECP IgY and serum anti-flagella IgY was significantly higher in the CN groups than in the CTRL group (P<0.05) at 21- and 17-days post hatch, respectively. The recall response in splenocyte PBMCs was significantly higher by 60% and 56% in the CN group than in CTRL group when stimulated with 0.25 mg/ml and 0.5 mg/ml antigen, respectively. Toxin neutralization by serum from CN and CT group was on average 40% higher than CT group at 17 days post hatch.

Chitosan nanoparticles loaded with extracellular proteins of *C. perfringens* and *Salmonella* flagellar proteins are safe and stable in vitro. These chitosan nanoparticles also induce cellular and humoral immune responses when administered to broiler chickens by oral gavage.

Further research will determine the nature of immune response to the different antigens in the crude mixture. Also, further research will determine the protective efficacy of chitosan nanoparticle vaccines against clostridial enteritis under field conditions, including applying chitosan loaded with *Clostridium perfringens* extracellular proteins to necrotic enteritis challenge studies.

Example 3

Mucosal Immunity of Broilers Vaccinated with an Oral Polyanhydride-Nanoparticle Based *Clostridium perfringens* Vaccine Expressing *Salmonella enterica* Flagella Two-separate studies were performed to analyze the protective effects of an oral polyanhydride-based *Clostridium perfringens* nanoparticle vaccine (PNP) loaded with inactivated *Clostridium perfringens* crude supernatant protein and surrounded by *Salmonella enterica* flagella. Study A constituted a complete randomized design of 3 treatments with 6 replicates. Day-hatched male Cobb-500 broilers (n=30) were orally gavaged with PBS (mock-vaccination) or 50 ug/0.5 ml of polyanhydride-based *C. perfringens* inactivated supernatant toxin vaccine (PN) or polyanhydride-based *C. perfringens* inactivated supernatant toxoid vaccine (PT). Boosters were administered at 3, 7- and 14-days post-hatch. Study B comprised a complete randomized design of 2 treatments with 6 replicates (n=6): Unimmunized or PN-vaccinated. Results of study A and B demonstrated no significant differences in BWG and FCR between treatments. Similarly, no significant differences were observed in ELISA IgA and IgY-specific anti-CP supernatant protein. Study A revealed ex-vivo toxin neutralization significantly higher percentage (P=0.0024) of neutralizing antibodies in PT treated broiler sera compared to PBS and PN. No significant differences were observed in ELISA IgA and IgY-specific anti-*Salmonella* flagellin protein between treatments at different ages. The proliferation of T-cells stimulated with 0.05, 0.1, 0.25 and 0.5 mg/ml of antigen was significantly increased (P<0.05) in PN vaccinated birds via splenocyte recall response. In study B, higher percentage (P=0.0487) of CD4+CD8+ population was found in caecal tonsils of PN vaccinated birds compared to control. *C. perfringens* DNA load in caecal contents demonstrated a significant decrease (P=0.0220) of CP bacterial population in broilers treated with PN vaccine when compared to control. PNP-*C. perfringens* candidate vaccines were safe with no systemic reactions or adverse effects on bird performance and immunogenic via the oral gavage route of administration.

Example 4

Chitosan Nanoparticles as an Intervention Strategy for Necrotic Enteritis in Poultry Necrotic enteritis (NE) in poultry is a severe *Clostridium perfringens*-induced disease of the gastrointestinal tract of birds. Both acute and chronic forms of infection lead to economic losses estimated to be around 3 billion USD annually. The chronic damage of NE has huge economic costs, including lower bird performance, veterinary and cleaning costs, increased condemnations, and animal deaths. Like every other disease, the host, pathogen, and environment interact in a myriad of complex ways to cause the disease. For example, poor ventilation, high stocking density, and/or heat stress can compromise gut microbiome, reduce innate immune responses, and cause increased accumulation and infection rates leading to necrotic enteritis. Environmental conditions include litter, ventilation, stocking density, season, and feed and water conditions. Host factors include genetics, age, immune status, and microbiome. Pathogens include *Eimeria, Clostridium, Salmonella*, and other possible pathogens. On the pathogen side, the *Eimeria-clostridium* combination is one of the most important dynamics of NE and is the subject of many current studies. Current intervention strategies include improved husbandry and biosecurity, vaccination, feed, and water additives, in-ovo innovations, and anticoccidial drugs. Currently greater than twenty-five live attenuated anticoccidial vaccines are available.

Figure 12:
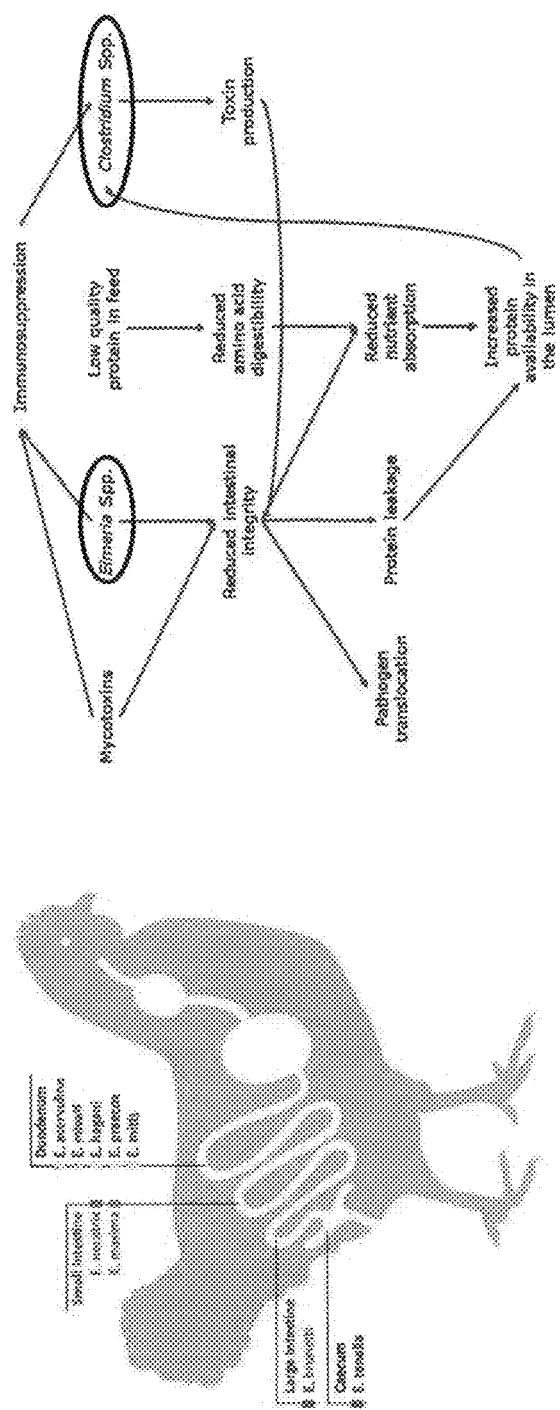
FIG. 12. An image of the host, pathogen and environment relationship involving *Eimeria* and *Clostridium perfringens* that culminates in reduced gut integrity associated with necrotic enteritis. *Eimeria* is an apicomplexan parasite that invades poultry enterocytes and can cause coccidiosis. Over nine strains of *Eimeria* infect poultry.

*Clostridium perfringens* is a gram positive non-motile rod, having 5-7 major toxin groups. It is anaerobic and commensal, usually found in the ceca and lower GI tract. A remarkable feature of pathogenic strains of *C. perfringens* is how fast they multiply under the right conditions. FIG. 12 is an illustration of the host, pathogen, and environment relationship involving *Eimeria* and *Clostridium perfringens* that culminates in reduced gut integrity. *Eimeria* is an apicomplexan parasite that invades poultry enterocytes and can cause coccidiosis. Over nine strains of *Eimeria* infect poultry. *Eimeria maxima* is one species most commonly associated with necrotic enteritis. Chickens almost always live with *Eimeria* infections, with healthy birds being generally able to keep them in check.

Figure 13:
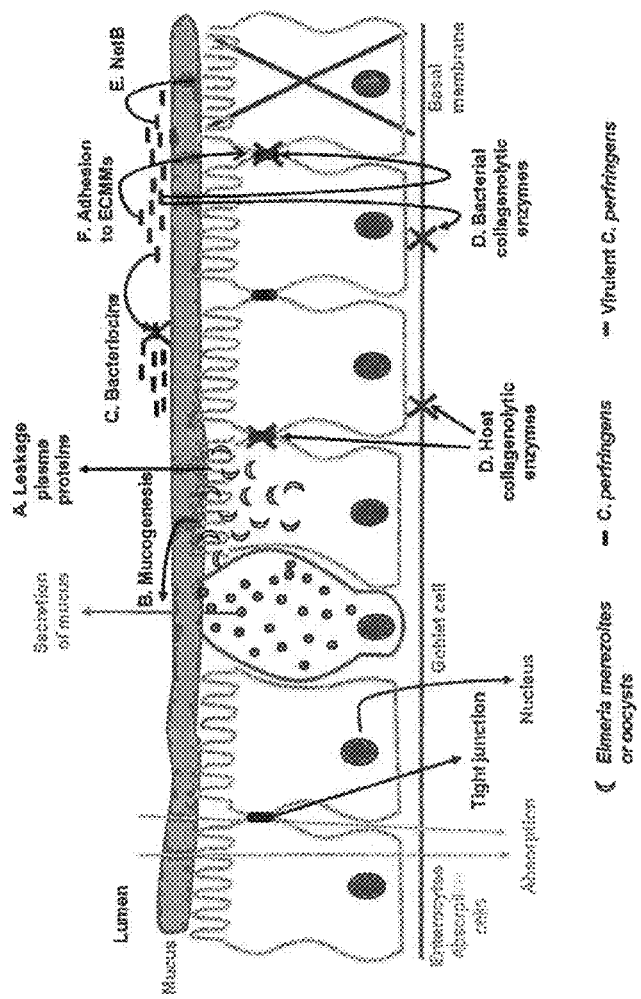
FIG. 13. Pathogenesis of necrotic enteritis (NE).
Figure 14A:
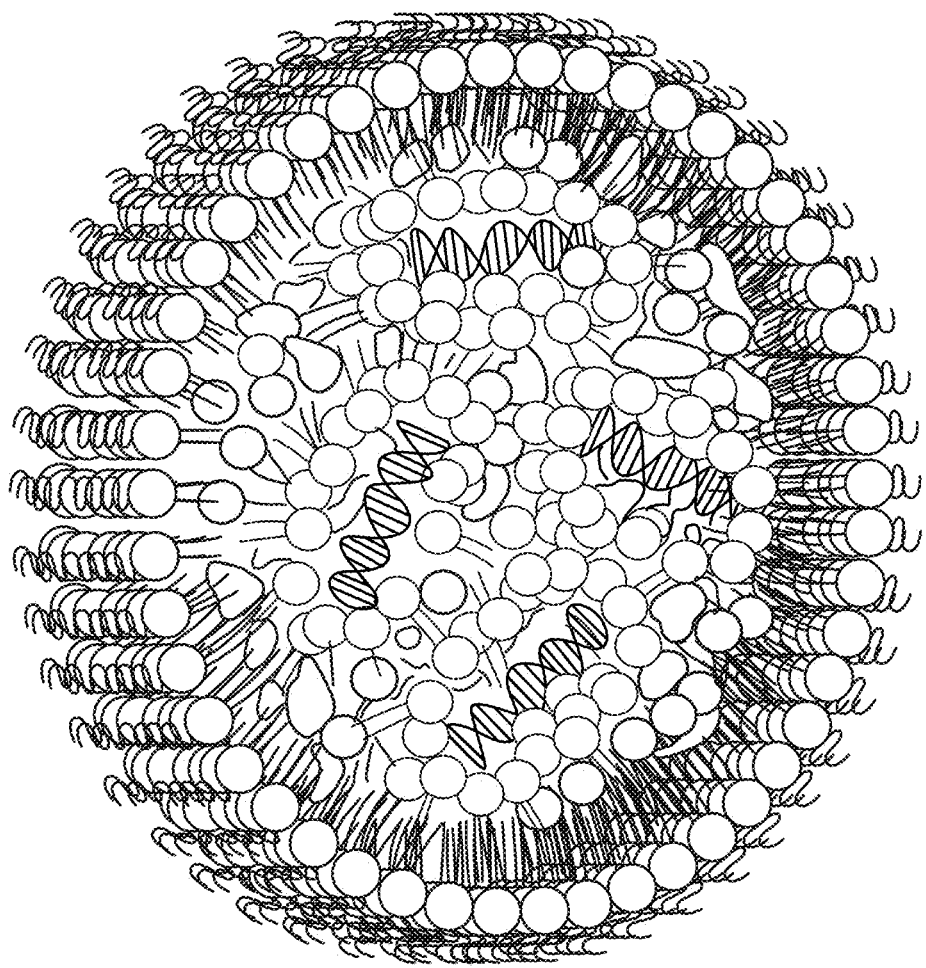
FIGS. 14A to 14C. Nanotechnology.
Figure 14B:
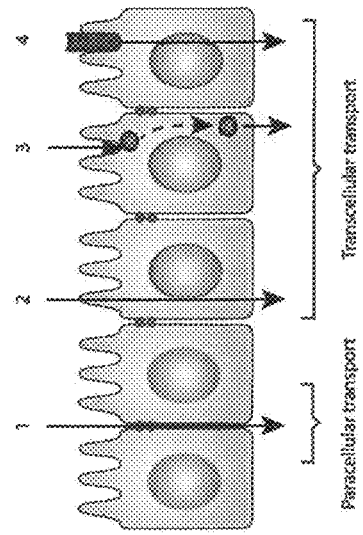
Figure 14C:
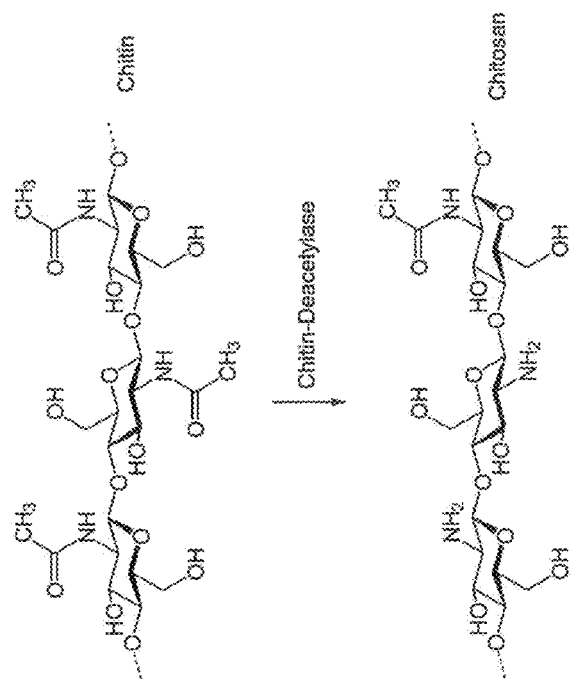
Figure 15:
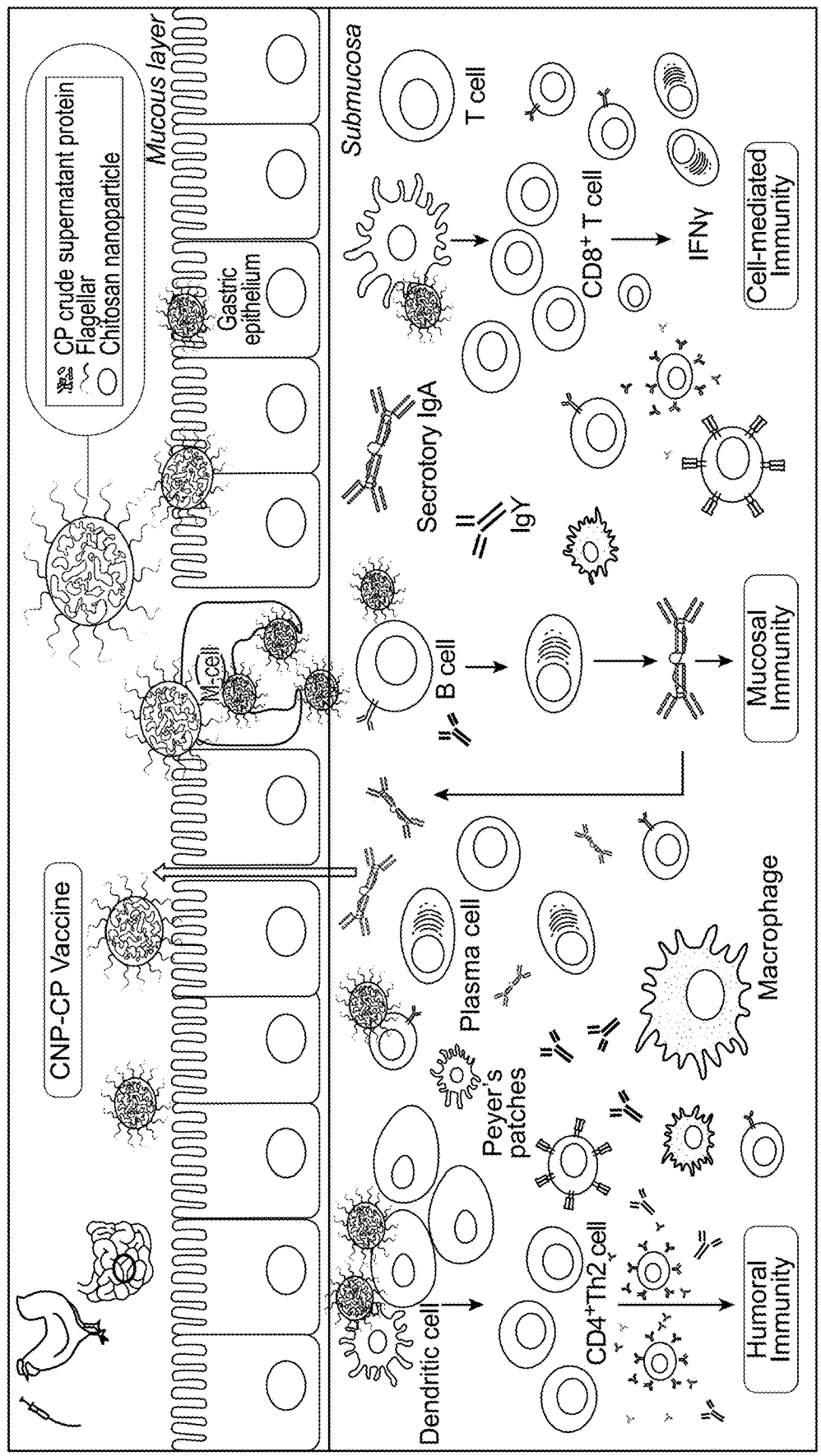
FIG. 15. Interaction of chitosan nanoparticles with the gut.
Figure 16:
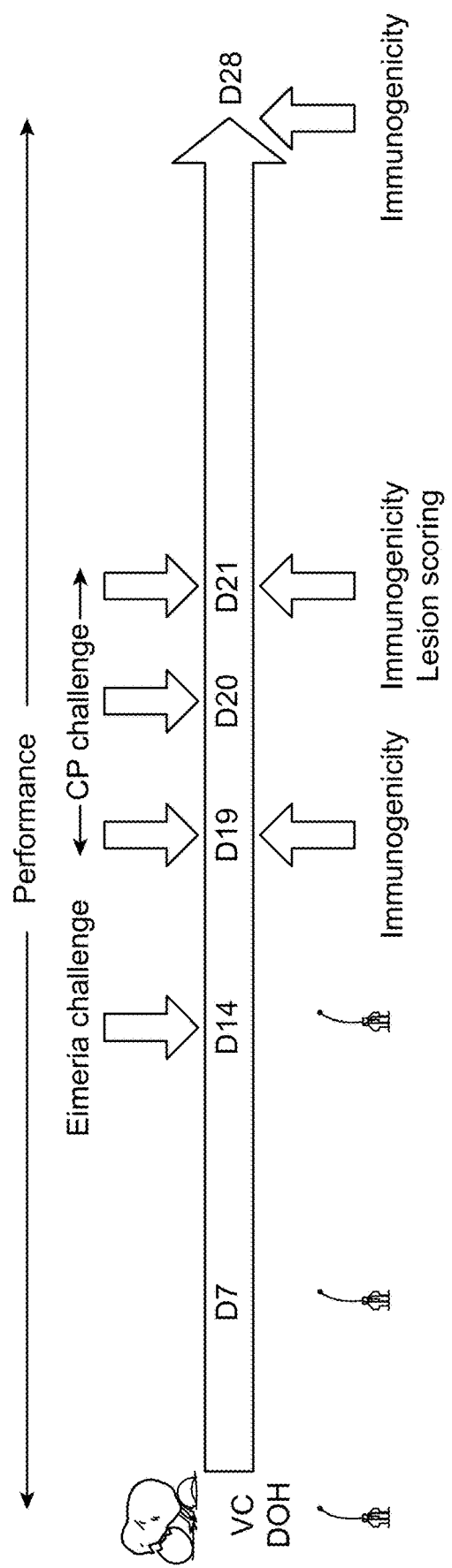
FIG. 16. Immunogenicity and Protection by Chitosan nanoparticle vaccine. Treatments are as follows: "NVNC (−ve Control) is no vaccine and no challenge; "VC" is vaccine with challenge; "NVC" is no vaccine with challenge. For the statistical analysis (SAS™ Proc glm, Ch-Sq (One-way)), N=6 (8 chicks/cage), preplanned contrast and P<0.05.
Figure 17B:
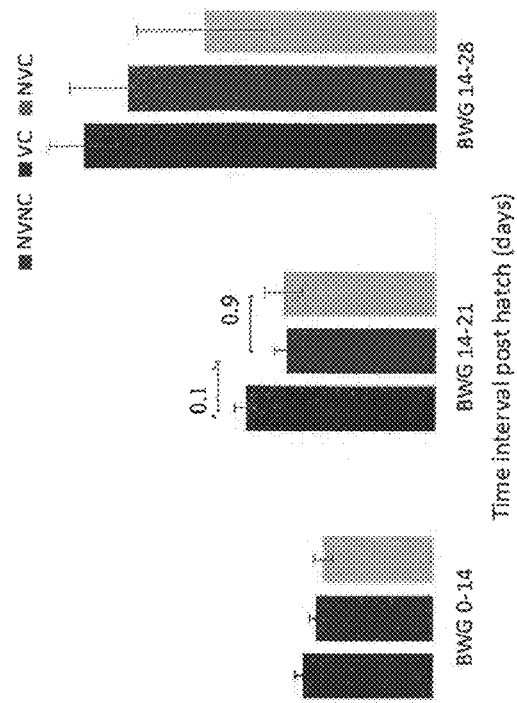
FIGS. 17A and 17B. Performance.
Figure 17A:
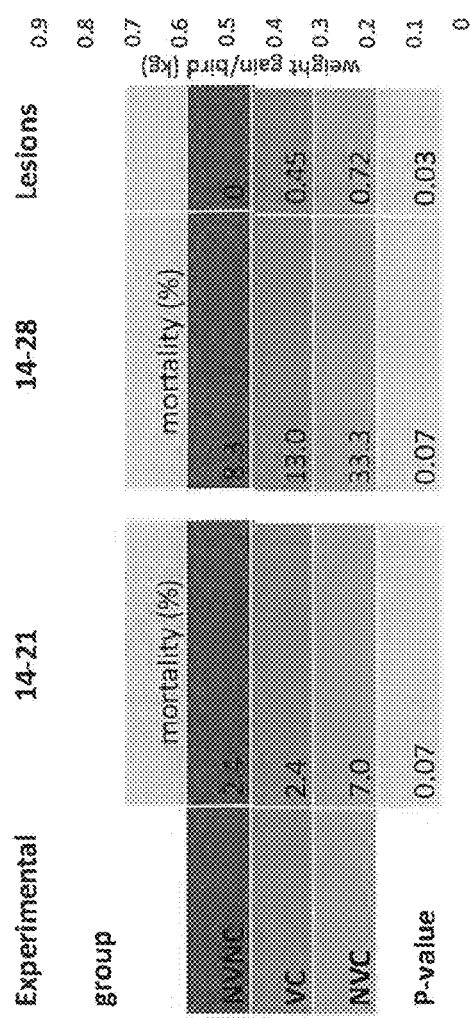
Figure 18B:
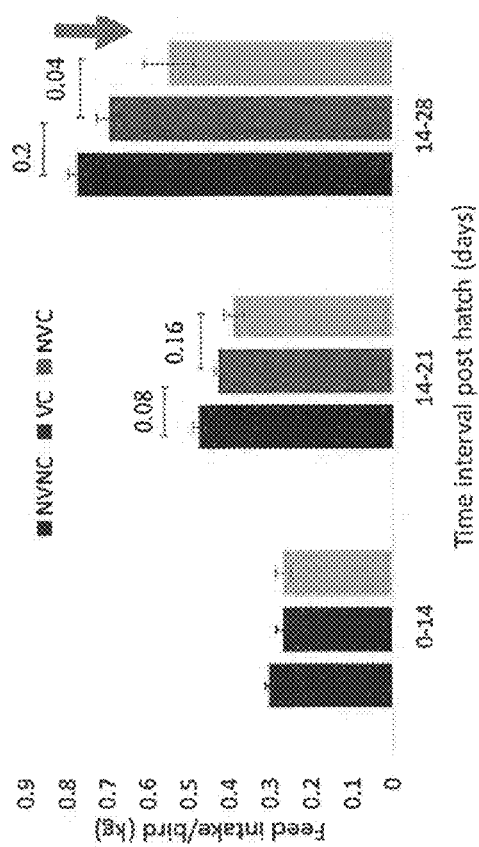
FIGS. 18A and 18B. Performance.
Figure 18A:
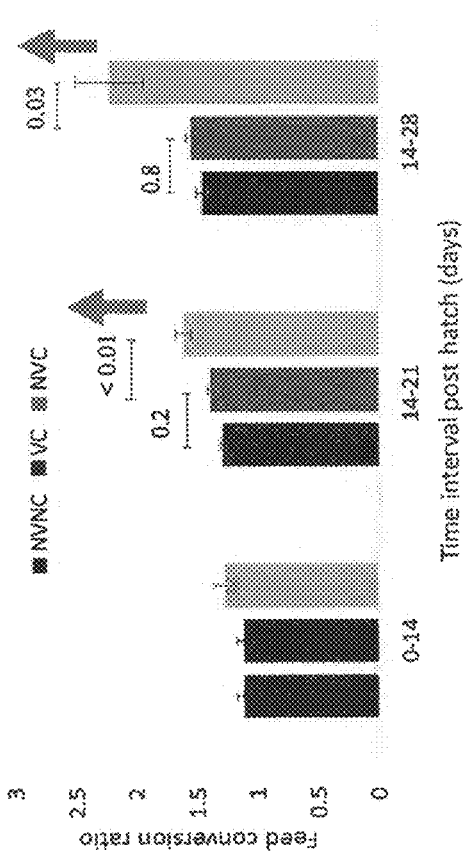
Figure 19A:
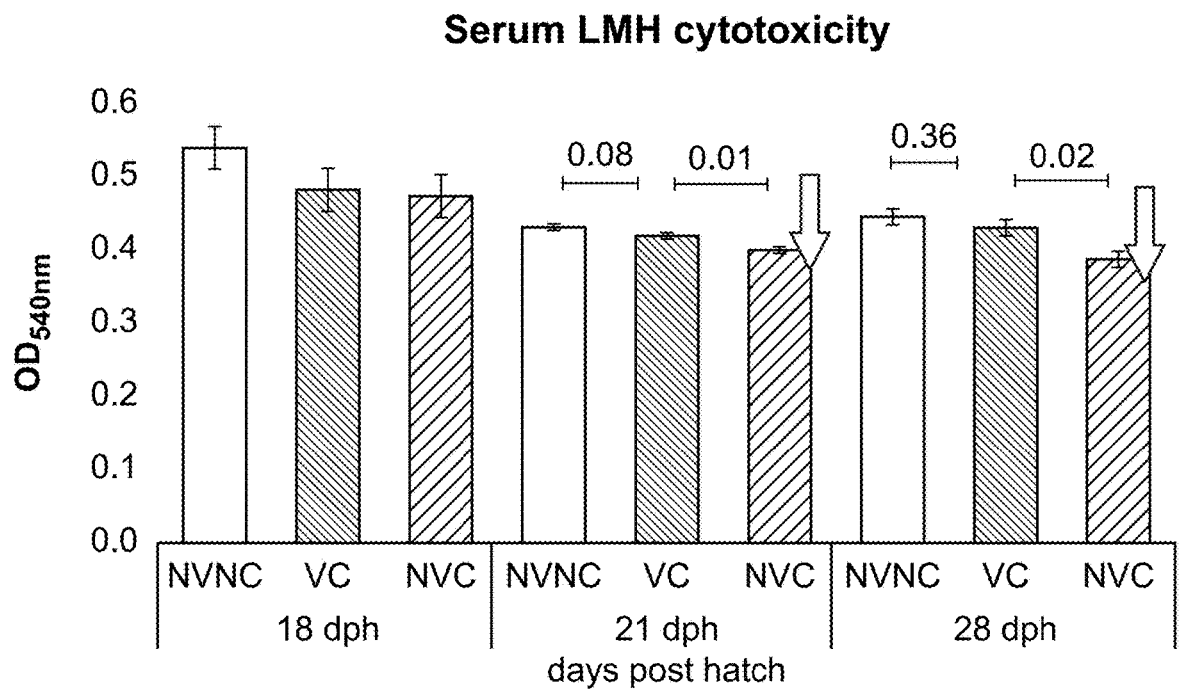
FIGS. 19A and 19B. LMH cytotoxicity.
Figure 19B:
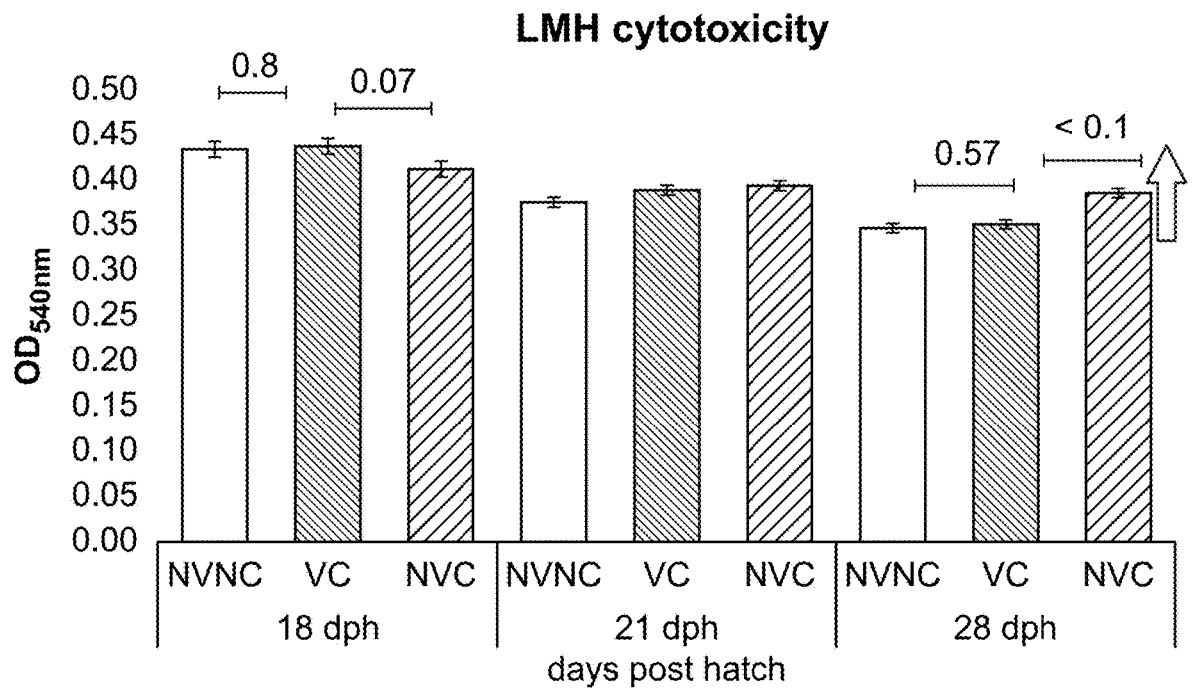
Figure 20A:
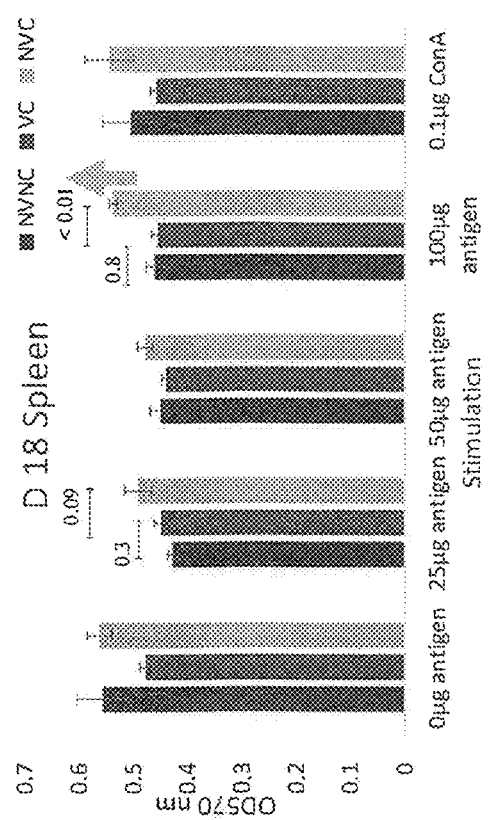
Figure 21:
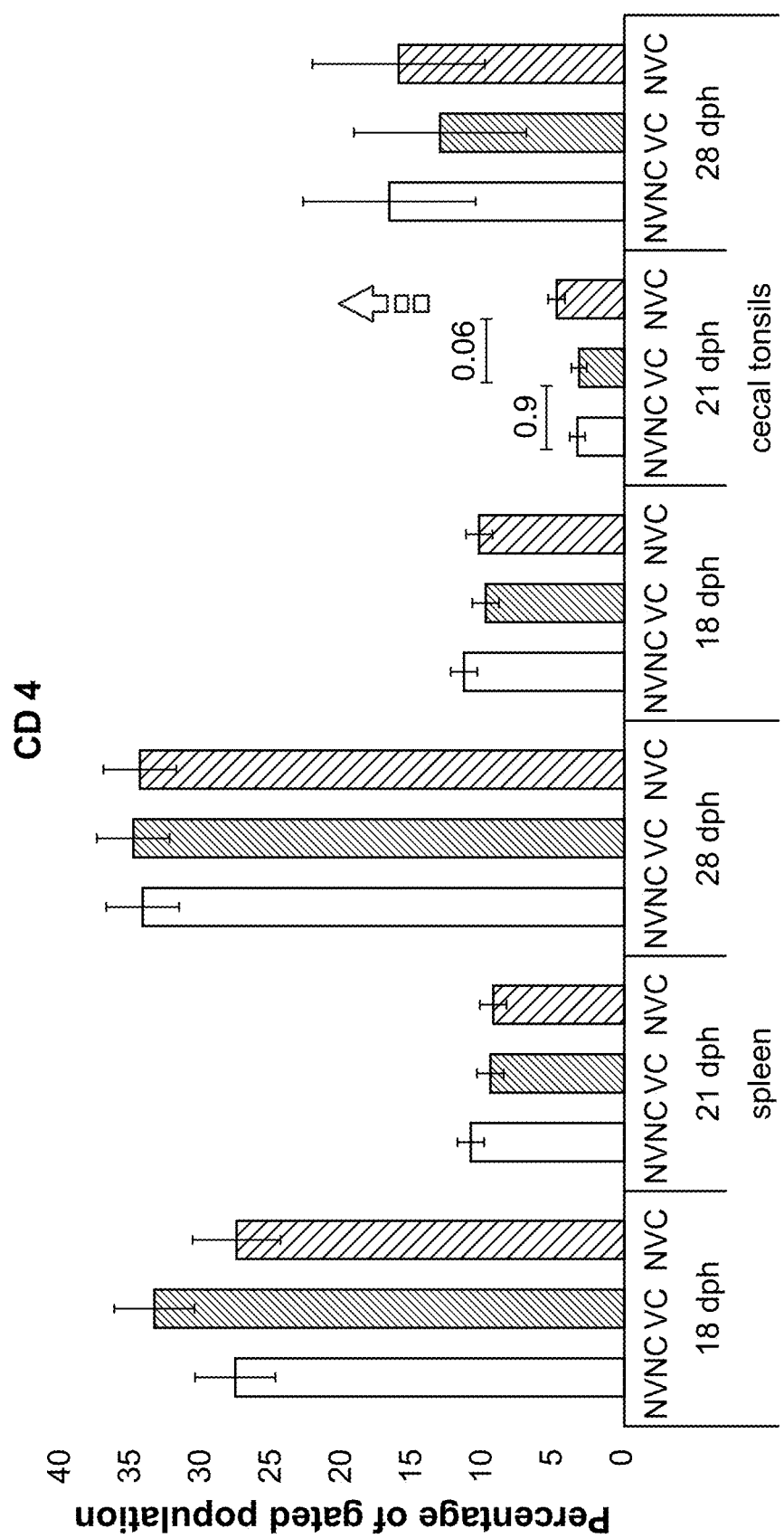
FIG. 21. CD4 T cell response.
Figure 22:
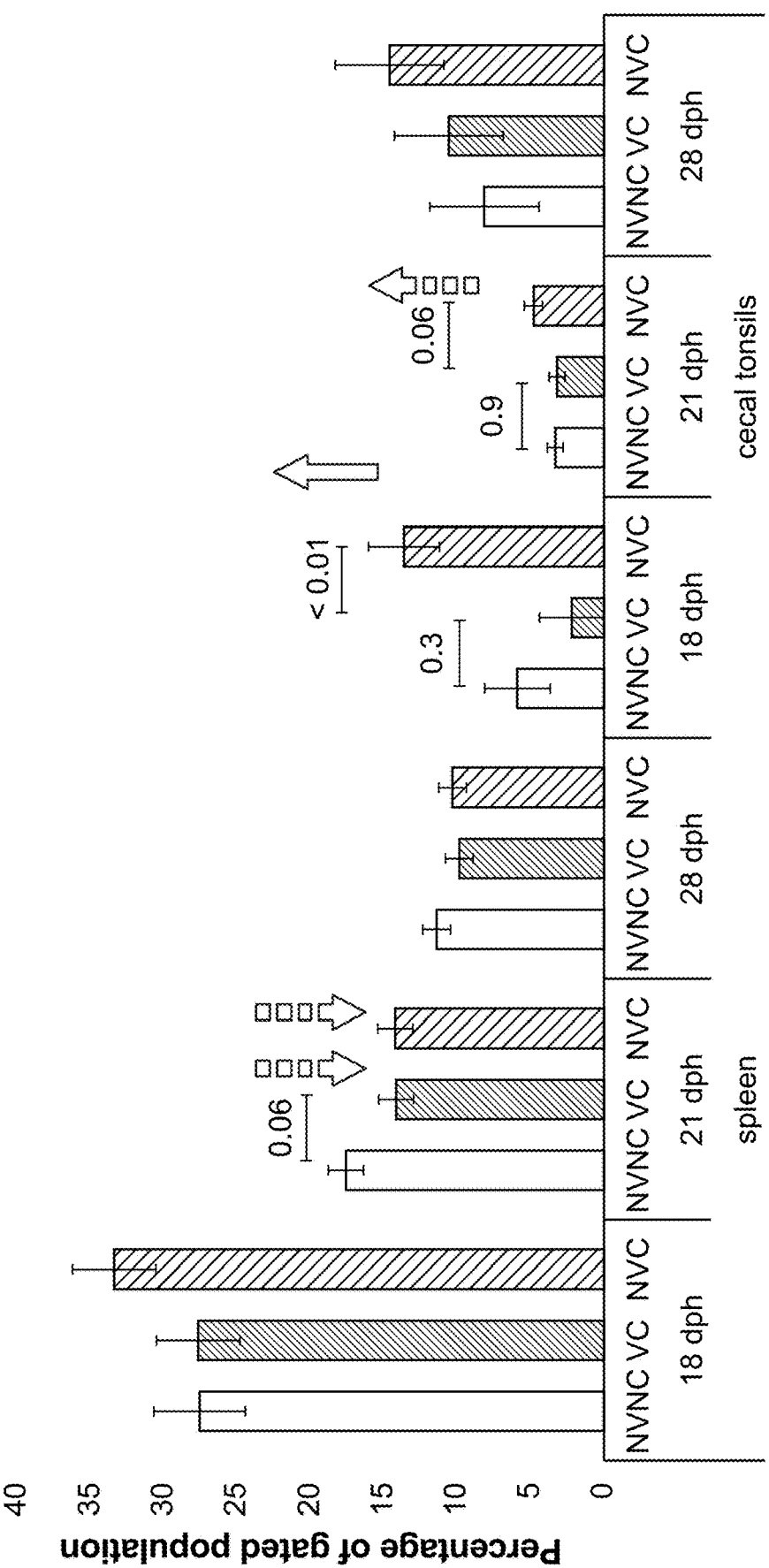
FIG. 22. CD8 T cell response.
Figure 23:
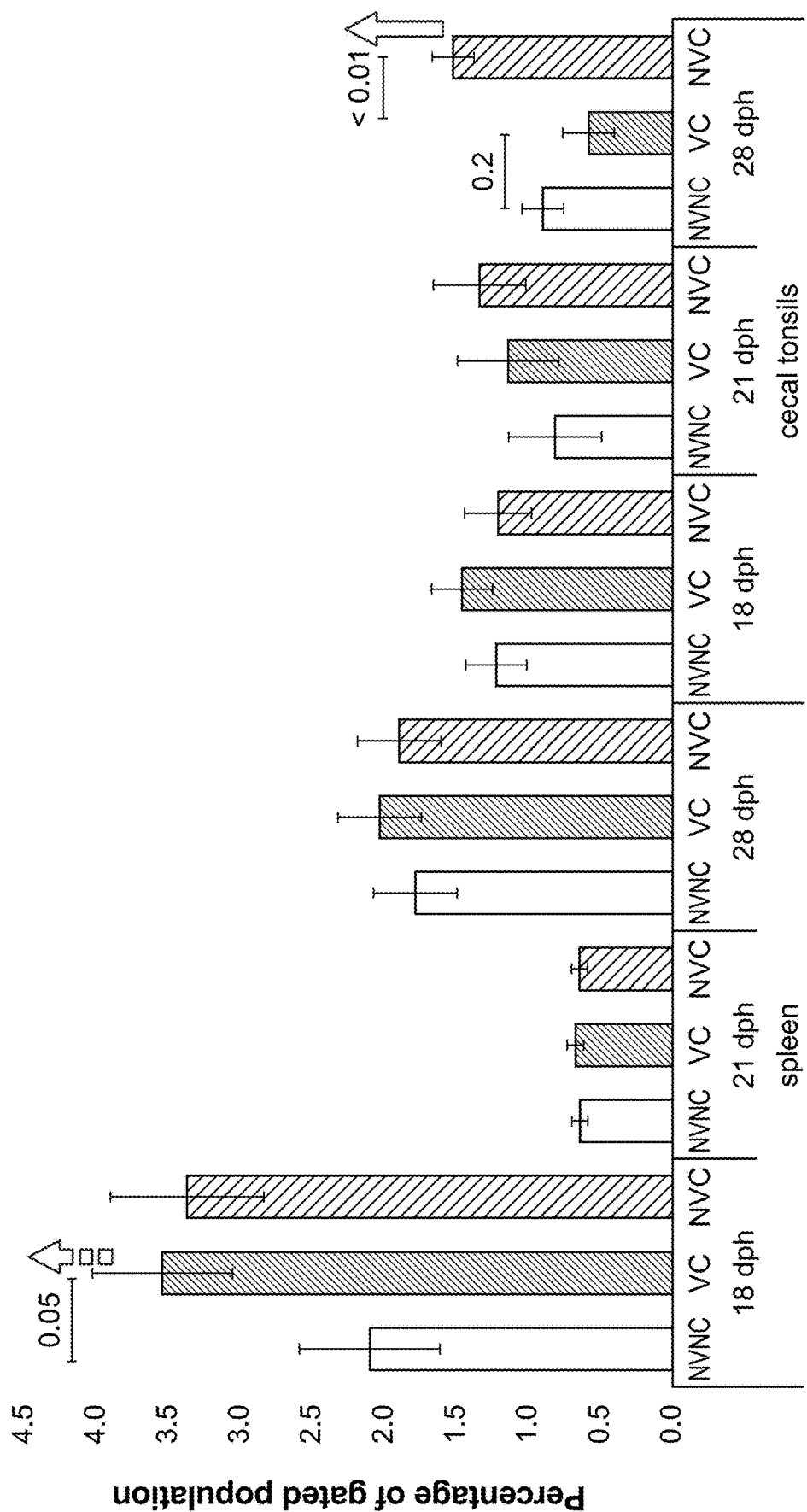
FIG. 23. CD4/CD8 T cell ratios.

As *Eimeria* merozoites invade enterocytes, they release plasma proteins which serve as food for virulent and opportunistic commensal *Clostridium*. *C perfringens* releases toxins that further damage the intestinal villi and gut tight junction proteins. Extensive damage to the gut wall, discolored liver, ruffled feathers, and bloody diarrhea are some symptoms associated with the disease (Timbermont et al., 2011, *Avian Pathol;* 40(4):341-7). FIG. 13 is a schematic of the pathogenesis of necrotic enteritis (NE).

Of the current intervention strategies, biosecurity and good management practices are the most important ways to reduce NE. Current vaccination efforts are largely aimed at controlling coccidiosis. Feed, water, and in-ovo supplements aim to boost innate and adaptive responses to infection but have variable protective efficacies. Anticoccidial drugs again are aimed at controlling coccidiosis and have been very effective. However, ionophores for example are classified as antibiotics because of their mode of action and subject to regulation. Also, resistant strains are emerging, necessitating the introduction of shuttle or rotational programs. Previous attempts to prevent broiler necrotic enteritis by vaccination have been handicapped by the practical limitations of broiler vaccination.

Previous attempts to prevent broiler necrotic enteritis by vaccination have been handicapped by the practical limitations of broiler vaccination. Live antigens are generally more immunogenic than subunit antigens. However, vaccination with live antigens include risk of reversion to virulence, negative public perception, interference by maternal antibodies. These limitations apply to current anti coccidia vaccines and anti-*C. perfringens* vaccines which are still largely being researched. Unlike long-lived birds, it is not practical to inject tens of thousands of commercial broilers after they have been placed, let alone give multiple doses. A single dose of vaccine administered in-ovo, in the hatchery or through feed and water in placed birds is ideal to reduce costs and maximize efficiency.

Unsurprisingly given its complex etiology, there is no consistency in infection models used by researchers, and the correlates of protection are therefore poorly defined. Unfortunately, orally administered, non-adjuvanted and unencapsulated subunits are inactivated or digested before they can get to inductive centers of the gut.

Delivery via nanoparticles may be helpful. The application of nanotechnology in poultry science is novel compared to other industries. Nanoparticles are non-toxic, biodegradable compounds whose size, shape, degradation behavior and other physicochemical properties can be adjusted to suit different applications. Nanoparticle sub cellular size and large surface area to volume ratio enhance their ability to penetrate physical barriers and phagocytosis. Compared to soluble antigens, a 30-fold increase in uptake has been recorded. As a matter of fact, one of the current leading COVID-19 vaccine candidates is based on a lipid nanoparticle encapsulating spike mRNA. The innovation of this study was to use nanoparticles as encapsulating agents to protect our subunit antigen, thus facilitating antigen delivery to immunological centers of the gut mucosa.

Figure 24A:
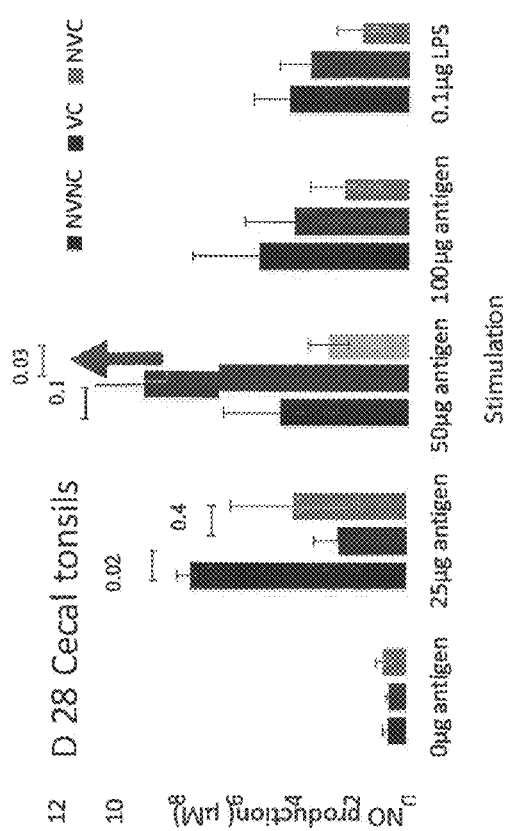
FIGS. 24A and 24B. Cecal tonsils nitric oxide production.
Figure 24B:
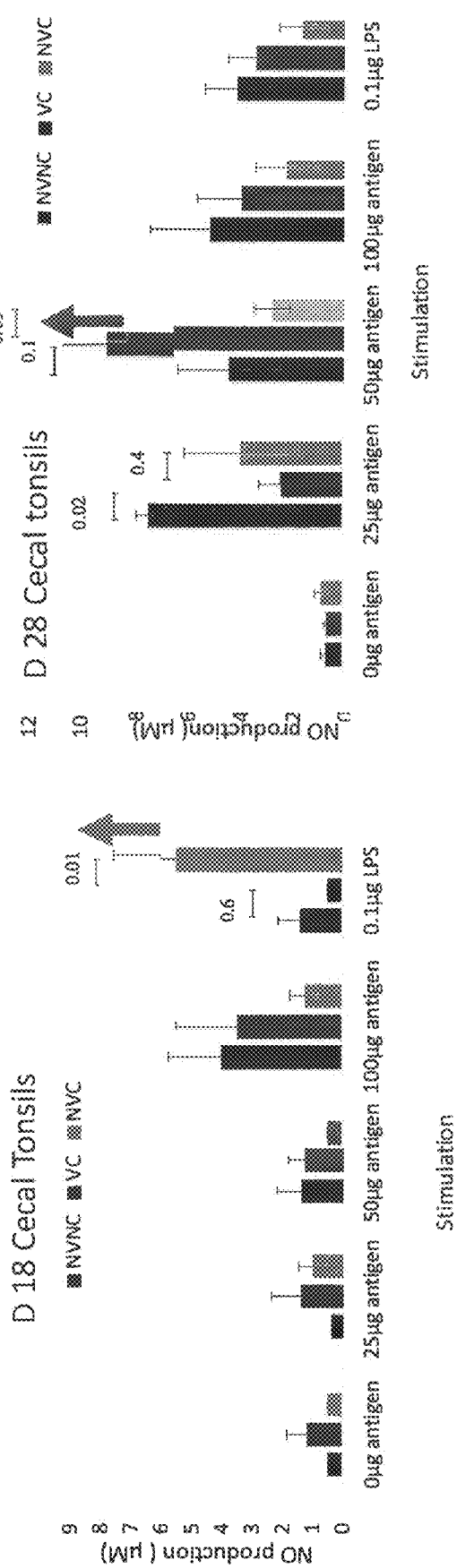

FIG. 14A is a schematic of a nanoparticle. FIG. 14B shows the chemical structure of chitosan, a derivative of chitin. As shown in FIG. 14C, chitosan is cationic and when combined with a polyanion tripolyphosphate can cross the gut to submucosa.

This example used chitosan nanoparticles. Chitosan is a derivative of chitin, a naturally abundant cell wall component of crustaceans, fungi, and so on. It is cationic and combined with the polyanion tripolyphosphate can cross the gut to submucosa. Such nanoparticles may be less than 500 nm in size and have many useful properties—they may act as vaccine adjuvants, their physicochemical properties can be modified, and they are already extensively used in pharmaceutical and medical applications.

FIG. 15 shows the interaction of chitosan nanoparticles with the gut, showing that nanoparticle encapsulated antigen will attach to epithelial cells and with help of M cells and scavenging dendritic cells will be transported to the submucosa. In the Payer's patch, antigen presenting cells will take up the nanoparticles and together with T cells and B cells stimulates an immune response.

This example explored the immunogenicity and protective efficacy of a chitosan nanoparticle vaccine loaded with crude extracellular proteins of C. *Perfringens* and *Salmonella* flagella in a necrotic enteritis in a NE challenge model.

To determine immunogenicity and protection by a chitosan nanoparticle vaccine, broiler birds were raised from day of hatch to d 28 in wire cages. There were 3 treatment groups: one non-vaccinated, non-challenged control; one group vaccinated with 50 μg CN nanoparticles in 0.5 ml PBS and challenged, and a last non-vaccinated challenged group. The challenge was an oral gavage of 5000 oocysts of *Eimeria* on d 14 followed 3 consecutive administration of log 8 cfu/ml *clostridium* on d 19, 20, and 21 post hatch. Vaccination or mock vaccination and necropsy for immunogenicity and lesion scoring were carried out at the indicated time points.

FIG. 16 shows immunogenicity and protection by a chitosan nanoparticle vaccine. The methods for assaying immunogenicity and protection by chitosan nanoparticle vaccine include methods as described in more detail in the previous examples. Treatments are as follows: "NVNC (–ve Control) is no vaccine and no challenge; "VC" is vaccine with challenge; "NVC" is no vaccine with challenge.

To assay nitric oxide production, adherent splenocytes stimulated with ion 0.05, 0.1, 0.25, or 0.5 mg/ml ECP or 10 μg/ml LPS and incubated for 96 hours prior to performing a Greiss Assay for NO production and optical density measurement at 540 nm taken.

Results

Performance. At one-week post infection, the % mortality in the negative control and vaccinated group were similar and less than mortality in the non-vaccinated, challenged group. At two-weeks post infection, % mortality had increased in the vaccinated birds but was still lower than non-vaccinated, challenged birds. Lesions scores were also lower in the vaccinated group compared to non-vaccinated, challenged group. There was no effect of treatment on body weight gain at the time points assayed. As shown in FIG. 17A, vaccinated birds had smaller lesions and less mortality than non-vaccinated birds. As shown in FIG. 17B, there was no effect of treatment on weight gain at one- and two-weeks post infection.

Feed conversion was significantly higher in the non-vaccinated, challenged birds at one week and two weeks post infection when compared to vaccinated challenged birds. Feed intake was lower in the non-vaccinated, challenged birds only at two weeks post infection. As shown in FIG. 18A, vaccinated birds had smaller lesions and less mortality than non-vaccinated birds. As shown in FIG. 18B, vaccinated birds had greater feed intake than non-vaccinated birds.

LMH cytotoxicity. As shown in FIG. 19B, LMH cytotoxicity in bile and ECP was higher in non-vaccinated, challenge birds.

Decreased cytotoxicity or increased toxin neutralization was found only in the serum of non-vaccinated, challenged birds compared to vaccinated, challenged birds. In bile, the reverse was the case, with decreased neutralization or increased cytotoxicity found in non-vaccinated, challenged birds. As shown in FIG. 19A, LMH cytotoxicity in serum and ECP was lower in non-vaccinated, challenge birds. As shown in FIG. 19B, LMH cytotoxicity in bile and ECP was higher in non-vaccinated, challenge birds.

Recall response. On day 18 post hatch (FIG. 20A), recall response was higher in non-vaccinated, challenged birds. On day 21 post hatch (FIG. 20B), vaccinated birds recorded higher recall response. By day 28 (FIG. 20C), T cells from non-vaccinated, challenge birds recorded a higher recall response compared to vaccinated birds. Antigen dependent increase in recall response is observe mostly in non-vaccinated challenged birds. FIG. 20A shows results from D18 spleen. FIG. 20B shows results from D21 spleen. FIG. 20C shows results from D28 spleen.

CD4 Response. As shown in FIG. 21, there was an increase in CD4 T cells at 28 dph in the non-vaccinated, challenge birds. Otherwise, not much difference was observed in the expression of CD4 T cells except in the non-vaccinated challenge group, approaching significance.

CD8 Response. Differences in the CD8 population between treatments were more pronounced, especially in the cecal tonsils. In the spleen there appeared to be a drop in the CD8 population of non-vaccinated and vaccinated challenged birds. While in the cecal tonsils, non-vaccinated challenged birds appeared to have higher % of CD8 cells. As shown in FIG. 22, there was an increase in CD8 T cells at 18 and 21 dph in the cecal tonsils of non-vaccinated, challenged birds.

CD4:CD8 Ratio. The CD4:CD8 ratio was calculated and found to be higher in the spleen of vaccinated birds compared to control. In the cecal tonsils on day 28 post hatch, this ratio was higher in non-vaccinated, challenged birds compared to vaccinated birds. As shown in FIG. 23, there was as an increase in the CD4/CD8 at 28 dph in the non-vaccinated, challenge birds.

Nitric Oxide Production by Cecal Tonsils. FIG. 24A shows nitric oxide (NO) production at 18 dph. FIG. 24B shows NO production at 28 dph. Nitric oxide production was found in the cecal tonsils in response to different stimulus and antigen concentrations. LPS stimulation up regulated NO production at day 18 post hatch in non-vaccinated, challenged birds compared to vaccinated birds. By day 28 however, vaccinated birds up regulated nitric oxide production. As shown in FIG. 24A, NO production was higher only in non-vaccinated, challenged birds at 18 dph. As shown in FIG. 24B, NO production was higher in non-vaccinated, non-challenged birds at 28 dph.

Splenic Nitric Oxide Production. In the spleen, nitric oxide production was up regulated in response to ECP in non-vaccinated, challenged birds. NO production was higher only in non-vaccinated, challenged birds at 28 dph. This is shown in FIG. 25.

DISCUSSION

This example demonstrates the successful induction of necrotic enteritis as observed by mortality figures and lesion scores in vaccinated vs non-vaccinated birds. Importantly, there was some protective effect of vaccination, the vaccine produced cell mediated immune response in the birds, and there were temporal, spatial, and antigen-dependent responses in NO production, increased at day 18, then decreased at day 28. While by the termination of this example there was no effect of treatment on weight gain, there was some protective effect as measured by FCR, and FI. For a majority of parameters assessed, the vaccinated challenged bird cluster with the negative controls.

It has long been established that cell-mediated immunity, rather than humoral responses are important for controlling *Eimeria* infections. The NE challenge model of the present example examined the protective role of antibodies against extracellular antigens such as toxins secreted by challenge *C. perfringens* strains. For example, NetB has been shown to be partially protective against NE in broilers.

In vitro serum coccicidal assays have demonstrated that compliment mediated killing of *Eimeria* merozoites is possible. Unexpectedly, vaccinated birds and negative controls appeared to have similarly fewer neutralizing antibodies in serum. This raises the possibility of other factors being at play here.

In fact, vaccinated birds clustered with non-vaccinated non-challenged controls for a good number of the immunological parameters assayed. This can be interpreted in two ways: either the wrong parameters in the wrong tissues at the wrong time are being assayed, or this lack of response has a direct implication in the partially protective efficacy of the vaccine. Some studies correlate the pathophysiology of coccidiosis with peak lesions. Is this the same with necrotic enteritis? A more holistic approach is required to study the underlying mechanism of protection of this vaccine.

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

What is claimed is:

1. A composition comprising:
    one or more *Clostridium perfringens* extracellular proteins; and
    a chitosan nanoparticle;
    wherein the one or more *Clostridium perfringens* extracellular polypeptides is entrapped within the nanoparticle.

2. The composition of claim 1, wherein the one or more *Clostridium perfringens* extracellular proteins comprise proteins prepared from a *Clostridium perfringens* culture supernatant.

3. The composition of claim 1, wherein the *Clostridium perfringens* comprises type A, type B, type C, type D, or type E *Clostridium perfringens*.

4. The composition of claim 1, wherein the one or more *Clostridium perfringens* extracellular proteins comprise native polypeptides.

5. The composition of claim 1, wherein the one or more *Clostridium perfringens* extracellular proteins comprise inactivated polypeptides.

6. The composition of claim 1, wherein the one or more *Clostridium perfringens* extracellular proteins comprises one or more *Clostridium perfringens* toxins.

7. The composition of claim 1, wherein the one or more *Clostridium perfringens* extracellular proteins consists of one or more *Clostridium perfringens* toxins.

8. The composition of claim 6, wherein toxin comprises alpha toxin (CPA), beta toxin (CPB), epsilon toxin (ETX), iota toxin (ITX), perfringolysin O (PFO), enterotoxin (CPE), beta2 toxin (CPB2), or NetB toxin.

9. The composition of claim 1, wherein the nanoparticles are about 150 to 200 nanometers in diameter.

10. The composition of claim 1, further comprising a *Salmonella enteritidis* flagellar protein.

11. The composition of claim 10, wherein the *Salmonella enteritidis* flagellar protein is present on the surface of the nanoparticle.

12. The composition of claim 11, wherein the *Salmonella enteritidis* flagellar protein is conjugated to the surface of the nanoparticle.

13. The composition of claim 1, further comprising an adjuvant.

14. A pharmaceutical composition comprising the composition of claim 1 and a pharmaceutically acceptable carrier.

15. The composition of claim 1, formulated for oral delivery.

16. A method of generating an immune response to *Clostridium perfringens* in a subject, the method comprising administering a composition of claim 1 to the subject.

17. The method of claim 16, wherein the subject comprises a bird of the order Galliformes.

18. The method of claim 16, wherein administration comprises oral delivery.

19. A method for delivery of one or more *Clostridium perfringens* extracellular proteins to the mucosal membrane of the intestinal tract of a bird of the order Galliformes, the method comprising the oral administration of a composition of claim 1 to the bird.

* * * * *